United States Patent
Nezu et al.

(10) Patent No.: US 6,791,006 B2
(45) Date of Patent: Sep. 14, 2004

(54) LKB1 GENE KNOCKOUT MICE

(75) Inventors: Jun-Ichi Nezu, Ibaraki (JP); Asuka Ose, Ibaraki (JP); Kou-Ichi Jishage, Shizuoka (JP); Dieter E. Jenne, Neuried (DE)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 0 days.

(21) Appl. No.: 10/006,611

(22) Filed: Nov. 30, 2001

(65) Prior Publication Data

US 2002/0166137 A1 Nov. 7, 2002

Related U.S. Application Data

(63) Continuation-in-part of application No. PCT/JP00/03504, filed on May 31, 2000.

(30) Foreign Application Priority Data

May 31, 1999 (JP) .......................................... 11/153030

(51) Int. Cl.[7] ........................ A01K 67/027; C12N 15/00
(52) U.S. Cl. ............................. 800/18; 800/14; 800/21; 800/22; 800/25
(58) Field of Search ............................. 800/14, 18, 21, 800/22, 25

(56) References Cited

FOREIGN PATENT DOCUMENTS

EP          1 036 844 A1       9/2000

OTHER PUBLICATIONS

Wall, 1996, Theriogenology, vol. 45, pp. 57–68.*
Overbeek, 1994, "Factors affecting transgenic animal production," Transgenic animal technology, pp. 96–98).*
Orban, 1992, PNAS, vol. 89, pp. 6861–6865.*
Leonard, 1995, Immunological Reviews, vol. 148, pp. 98–113.*
Moens, 1993, Development, vol. 119, pp. 485–499.*
Griffiths, 1998, Microscopy Research and Technique, vol. 41, pp. 344–358.*
Mullins, 1990, Nature, vol. 344, pp. 541–544.*
Hammer, 1990, Cell, vol. 63, pp. 1099–1112.*
Mullins, 1989, EMBO J. vol. 8, pp. 4065–4072.*
Taurog, 1988, Jour. Immunol. vol. 141, pp. 4020–4023.*
Mullins, 1996, J. Clin. Invest., vol. 98, pp. S37–S40.*
Campbell and Wilmut, 1997, Theriogenology, vol. 47, pp. 63–72.*
McGreath, 2000, Nature, vol. 405, pp. 1066–1069.*
Kent–First, 2000, Nature Biotecnology, vol. 18, pp. 928–929.*
Dinnyes, 2002, Cloning and Stem Cells, vol. 4, pp. 81–90.*
Capecchi, 1994, Scientific American, vol. 270, pp. 34–41.*
Hemminki, 1998, Nature, vol. 391, pp. 184–187.*
Rombauts, S. et al. Computational approaches to identify promoters and cis–regulatory elements in plant genomes, Plant Physiology, 2003, vol. 132, pp. 1162–1176.*
Hemminki et al., "A serine/threonine kinase gene defective in Peutz–Jeghers syndrome", Nature, 391:184–187, 1998.
Jenne et al., "Peutz–Jeghers syndrome is caused by mutations in a novel serine threonine Kinase", Nature Genetics, 18:38–43, 1998.
Ylikorkala et al., "Vascular Abnormalities and Deregulation of VEGF in Lkb1–Deficient Mice", Science, 293:1323–1326, 2001.

* cited by examiner

*Primary Examiner*—Deborah Crouch
*Assistant Examiner*—Valarie Bertoglio
(74) *Attorney, Agent, or Firm*—Fish & Richardson P.C.

(57) ABSTRACT

A mammal is provided, in which the LKB1 gene can be deleted phase-specifically and tissue-specifically. These mammals are highly useful as tools to reveal the onset mechanism for diseases caused by LKB1 gene deficiency, such as Peutz-Jeghers syndrome and cancers, as well as to develop therapeutic agents, methods, and so on for the diseases.

3 Claims, 10 Drawing Sheets

GGAGATCCAGCTGCTGCGGCGGCTGCGGCATCGGAATGTGATCCAGCTTGTGGACGTGCTGTACAATGAGGAGAAGCAGA
AGATatatcctgtgggtggagtgggctgggtggccctgtgttaggggctggaagccttctgcaaggcctctggcagca
atagtgctacatgtcatcctgtggtgcctgtcagctcatcaggcaggggagcaaggcatggggcttccacctggtgccag
cctgttctgagcagtgtggctgggactgggcatggcctcacagggacttggggcctatgtacattgacagggccccggct
ggttctagaggtttccatgctgccccttcccagaggtagaggttgcacagcctacgttgcatctgggcagtcctgggagc
attctgagaacccagtgccctgcagccccaactcctggtacccatctctccctgtggctagtacaccagctgatttcagt
cctgttgtaatctatgctgactccatgtggtccaagtcactgtggtggtcttgtggaccctgtgagtactgatagggagc
gcagaatggcgggagagcagagtggtggtggtctgttggcccagcggggccctccagaccactgttgctaggagcagggc
tcctgggcttggtgtgctgctttccttagcgccctacGTATATGGTGATGGAGTACTGCGTATGTGGCATGCAGGAGATG
CTGGACAGTGTGCCGGAGAAGCGCTTCCCTGTGTGCCAAGCTCATGGgtgagtgccctgctgggtgcaggaggagcagcc
attgtcaggaaacccaggtgtttctgggcccccagttttttaacccagccaatgtgcttagggttaccctcttgttaggcc
ctgtggtcccgctgccctgcagagccatagtgggtctgagtcctgttcagtgctcccaggttcagcagaatcacatcccc
tggttagcagagaacaaagggaagggaagggaaggaagcaagccagaggggaaacctggctccctgggcctgggcagcag
tgactgccagttgccctgtgtaattttagtggcccagccttctgactctcaggtctgtttgcctgagccctaaacatcta
tcaccttgtaggccaggtctcatgagtctcccaaacttcatatcagacttatgtaggtaccatggtatgggctgagacac
tgtggggcctgagccagtcccacccattcagGTACTTCCGCCAGCTGATTGACGGCCTGGAATACCTACACAGCCAGGGC
ATTGTTCACAAGGACATCAAGCCGGGCAACCTGCTACTCACCACCAATGGCACACTCAAGATCTCCGACCTCGGTGTTGC
CGAGgtaggcaccatgtgcagggatcatgggccgcttctcctgagctgccctgactctcactgccctgcagGCCCTGCAC
CCTTTCGCTGTGGATGACACCTGCCGGACAAGCCAGGGCTCCCCGGCCTTCCAGCCTCCTGAGATTGCCAATGGACTGGA
CACCTTTTCAGGTTTCAAGGTGGACATCTGGTCAGCTGGGGTCACACTgtaagtgtcttgtgtgtaccctgtagcagatg
ggggctgtgggttttccctagtgttcttgggccttttttgcccacagtgtgtggctagcaggttggacattccaggtctg
tggggtgtggttcctcaccctaccccaccccactccacagggttttgcttgcacacagatgtaggtgccatgactgcacat
ctaccagttaacatgtgtcctgtctgggagttggggcacctgtcctctggtctccagtgtggccagcactgacactcttt
tcctatgtgaagTTACAACATCACCACGGGCCTGTACCCATTTGAGGGGGACAATATCTACAAGCTCTTTGAGAACATTG
GGAGAGGAGACTTCACCATCCCTTGTGACTGCGGCCCACCACTCTCTGACCTACTCCGAGgtgggcatctctaaatcacc
caaatgttaggacagcaagggacagagcccctggtctggagggttctgaccttactgtcaggacagcctttgtccgcca
ggatgggaggtttctgagattgcttccccccatctggggccggggtgggtgggtggggtctcagtgctatggggcctagg
aaggccaaggggatggatgctgtagtggtgctgtagcacaaagcaggcacctgctacactcacttatctcttctgtccta
cagGGATGTTGGAGTATGAGCCGGCCAAGAGGTTCTCCATCCGACAGATTAGGCAGCACAGgtgagcatggccggcctgt
ctcagcctgctgggggtctgagctgagaacatggtctcagaggtgctaggtcatcacaggagtaaggatcagtgtgctgt
gtgtattgatgtctgggaaggctgtgtgtgaacttggggtgtgacaggggtgcccaatgcaggcctccctacctttatca
ttttgttcaggagtgcaggcgttatgtggcctgagaagctgtagatttcagggcctagaattagagacggatcctcccat
ggtggggagggaggagtagatgggaagtgtcactttggatcccagctgttccttggccatctggacatggaaatgtgtc

```
tagggaggccaacaggaagcgtgaggcatggtgtctttcctcacctgaggctaagagccttctgggtaacagtggagcct
ctgtcctcccttttgtttatttaccagctggtcagagcctttgggtccaggcttctctgtcctcttctcccttcatgctag
actgagactggctcagctgggtgtcccccagtgagggcttctagcctatccgtgttcaaggcgggtgggactataggtgc
agggacctgattgcccaccctagtccaaggcgctgtggctgtcatcagtgggtggtggtttgtgccagtgctatgggtgt
taggctacctcaagcctgtagccggagcactaaggcctcgtcttatgtaaggacagccatggtgtgggcttttggtgggta
ttggccagccgtggtcacagtgcctggcacctgatgtctgtgctgcacttggccttctttagCTGGTTCCGGAAGAAACA
CCCTCTGGCTGAGGCGCTCGTACCTATCCCACCAAGCCCAGACACTAAGGACCGCTGGCGCAGTATGACTGTAGTGCCCT
ACCTGGAGGACCTGCATGGCCGTGCGGAGGAGGAGGAGGAGGAAGACTTGTTTGACATTGAGGACGGCATTATCTACACC
CAGGACTTCACAGTGCCTGgtaagctggcttggcgcagctcctactggagctggtgactttgtgcactctggggctggtc
cccttcccaagtctccagccagctaacatgagccaccaggactgccaaagccatcctggtggctgtggcatttcactctg
ggctagatgaagggctccctggctgcatctagcaggaggaggggaaccctggagggcagtgggtaggggccctgagacag
ccacctgagggagggtccagtggccctcggtcctggccatgcctgacctatatcgccttcttccccaggtgtcgaggag
gcggccgaggcagggcttagcgaggatgcatgcgacacatgcatgtggaagagccagggcgcaggccttcctggagagga
gcccgaggaggggtttggggctttagtgtagctccctgtctgctgccccacccatgtcctccataaagctttgtccactg
tgtctgcaggtggatgcttgccgcgacttccctcctgtcactaccctgacaggctccccaccagggtttcagagaacatg
cctgggtccaaggcctgagctaggtcctcagtgccagggtggccaccagccaggggctcttggggcctttgttcctgtgg
cctgcatgccagtcccacttagctcctggcctttcaaatagctttggtgggagggtaaggaccttgggctactgtgtctc
ctgtagcaattgagagttctaatagcagtgcccgctgggtgccaggtggaatccacaaggacaggtatacacctgatgtc
cagtatgggccttggccacagccctttctaaggtttaaagcatccctatgtgggaatagtgtcttctactctgtcacgtg
gagcccttgtctagactgtcccacaggctgggctcctggctgagagctggtttctctgctggggagaagatgtacttagg
tgctggttgcatgagggaccccttaaggctgctgtggtttgaaggaaggcaagggtctggggacactggttggccatggag
cccatttgtcaaatgggggtagtgttgcacagagtgaagtgaccgtgctctgaggatagcctgatccctctgtacttggca
tgagggtcggactctgcagcaacaggacaggggctttctactcagtgccttgtgtggaggaggggacagatgctttctca
gagtccacctgacctcaagcctcagtccatgcagagtgagccagagtgggtgctgctagtgtggccaagtcagagggtt
tgggagagaaattctggatccaggagcgtgggcagtgggctgtgtgctgggttccacagccgcattgccaagcactggac
tgtggagttacatgtagacactgacctctggagcctgggaagcttcaggagaggccatcttttgtcccactgcgagggca
ggccaacagagcaagctggtctgcagccctcagctggatgatctccttcccggtgctcatcgcagctagtagctcccagg
ccgaatgcttcatctccttgtgcctgtactgagggtctagagcctctcccttggagagctctgtgagctggtgctgggct
gcccaggctagacaggcaggtgagcgtgggcatgctgcaggagggccagggcatagcactgtgaaggcagtgggcctgct
tgcctttggagctactgaggggtgggtggcaccagaggctagagcacctccgaccagcctctgtcacagttggggctggc
tgggccctggggctttgagctacctgcccttggctcaagctatgcttgccatcttcccgtagGACAGGTCCTGGAAGAG
GAAGTGGGTCAGAATGGACAGAGCCACAGTTTGCCCAAGGCTGTTTGTGTGAATGGCACAGAGCCCCAGCTCAGCAGCAA
GGTGAAGCCAGAAGGCCGACCTGGCACCGCCAACCCTGCGCGCAAGGTGTGCTCCAGCAACAAGATCCGCCGGCTCTCGG
CCTGCAAGCAGCAGTGACTGAGGCCTACAGgtgggcatgggcctgggtccagccatccctggtgttcacagtgggtgtct
gctgggctcctagctccttcccgtagggcagtgctgcaagggggaaggtctggtggttgaggtggtactaagtgaccacc
cattctaccaacagTGTGTCATCAGGATCTCTGGGCAGGTGTCCCTGCAAGGCTGGGTTTTCCAGGCCTGCCTGTCCACT
```

CACTTCGGGACGTTGCAGCCGAGGGCGGACCTGCTGCCCCAGAAGCACTTTATGTCGAGACCACTGGCCGGCCTTGCCTG
CATGCCGCCCTGCGAGCCTCGCTGTCTTTGGGTTGGTTTCTTTTTTTTTAATAAAACAGGTGGATTTGAGCTATGGCTAT
GAGGGTGTTTGGAAATATGGAGCAGGCGGGGCACAGGGTGGCCTGCAGAGAAAACCCAGAGCAAACAAATATGCAGAGAC
ATTTATGATTAACCAGACAACACGACCAACCACAGAGGGCGCAGGGCAGGGAGTGGGCAGGCACTCACAGCGAGTCTGCC
CTATCTTTTGGCAATAAATAAAGCTTGGGAAACTTG

FIG. 4

F23 synthetic linker

5'      tgcgacacatggataccgctcgagtcg       3'
3'  acgctacgctgtgtacctatggcgagctcagcttaa  5'

AvaII    ClaI    XhoI   EcoRI loxP2 synthetic linker

SpeI HindIII         loxP ->                              EcoRI     BamHI                        loxP ->                        HindIII XhoI
5' ctagtcaagcttcataacttcgtataatgtatgctatacgaagttatcgaattcggatccataacttcgtataatgtatgctatacgaagttatcaagcttc    3'
3'     agttcgaagtatgaagcatattacatacgatatgcttcaatagcttaagcctaggtattgaagcatattacatacgatatgcttcaagttcgaag    5'

FIG. 6

SEQUENCE LISTING

```
<160> NUMBER OF SEQ ID NOS: 22

<210> SEQ ID NO 1
<211> LENGTH: 1795
<212> TYPE: DNA
<213> ORGANISM: Mus musculus
<220> FEATURE:
<221> NAME/KEY: CDS
<222> LOCATION: (51)...(1358)

<400> SEQUENCE: 1
aattcggatc caaggcggcc cgaaggacag aggacaaaga gtgggccagg atg gac          56
                                                        Met Asp
                                                          1 gtg gcg gac ccc gag ccg ttg ggc ctt ttc tcc gag ggc gag ctg atg       104
Val Ala Asp Pro Glu Pro Leu Gly Leu Phe Ser Glu Gly Glu Leu Met
          5                  10                  15 tcg gtg ggc atg gac acc ttc atc cac cgc atc gac tcc acc gag gta       152
Ser Val Gly Met Asp Thr Phe Ile His Arg Ile Asp Ser Thr Glu Val
     20                  25                  30 atc tac cag ccg cgc cgc aaa cgc gcc aag ctc atc ggc aag tac ctg       200
Ile Tyr Gln Pro Arg Arg Lys Arg Ala Lys Leu Ile Gly Lys Tyr Leu
 35                  40                  45                  50 atg ggg gac ctg ctc ggg gag ggc tcg tac ggc aag gtg aag gag gtg       248
Met Gly Asp Leu Leu Gly Glu Gly Ser Tyr Gly Lys Val Lys Glu Val
                 55                  60                  65 ctg gac tcc gag acc tta tgc cgc agg gcg gtc aag atc ctc aag aag       296
Leu Asp Ser Glu Thr Leu Cys Arg Arg Ala Val Lys Ile Leu Lys Lys
             70                  75                  80 aaa aag ctg cgc agg atc ccc aat gga gag gcc aac gtc aag aag gag       344
Lys Lys Leu Arg Arg Ile Pro Asn Gly Glu Ala Asn Val Lys Lys Glu
         85                  90                  95 atc cag ctg ctg cgg cgg ctg cgg cat cgg aat gtg atc cag ctt gtg       392
Ile Gln Leu Leu Arg Arg Leu Arg His Arg Asn Val Ile Gln Leu Val
    100                 105                 110 gac gtg ctg tac aat gag gag aag cag aag atg tat atg gtg atg gag       440
```

```
Asp Val Leu Tyr Asn Glu Glu Lys Gln Lys Met Tyr Met Val Met Glu
115                 120                 125                 130 tac tgc gta tgt ggc atg cag gag atg ctg gac agt gtg ccg gag aag        488
Tyr Cys Val Cys Gly Met Gln Glu Met Leu Asp Ser Val Pro Glu Lys
                135                 140                 145 cgc ttc cct gtg tgc caa gct cat ggg tac ttc cgc cag ctg att gac        536
Arg Phe Pro Val Cys Gln Ala His Gly Tyr Phe Arg Gln Leu Ile Asp
            150                 155                 160 ggc ctg gaa tac cta cac agc cag ggc att gtt cac aag gac atc aag        584
Gly Leu Glu Tyr Leu His Ser Gln Gly Ile Val His Lys Asp Ile Lys
        165                 170                 175 ccg ggc aac ctg cta ctc acc acc aat ggc aca ctc aag atc tcc gac        632
Pro Gly Asn Leu Leu Leu Thr Thr Asn Gly Thr Leu Lys Ile Ser Asp
    180                 185                 190 ctc ggt gtt gcc gag gcc ctg cac cct ttc gct gtg gat gac acc tgc        680
Leu Gly Val Ala Glu Ala Leu His Pro Phe Ala Val Asp Asp Thr Cys
195                 200                 205                 210 cgg aca agc cag ggc tcc ccg gcc ttc cag cct cct gag att gcc aat        728
Arg Thr Ser Gln Gly Ser Pro Ala Phe Gln Pro Pro Glu Ile Ala Asn
                215                 220                 225 gga ctg gac acc ttt tca ggt ttc aag gtg gac atc tgg tca gct ggg        776
Gly Leu Asp Thr Phe Ser Gly Phe Lys Val Asp Ile Trp Ser Ala Gly
            230                 235                 240 gtc aca ctt tac aac atc acc acg ggc ctg tac cca ttt gag ggg gac        824
Val Thr Leu Tyr Asn Ile Thr Thr Gly Leu Tyr Pro Phe Glu Gly Asp
        245                 250                 255 aat atc tac aag ctc ttt gag aac att ggg aga gga gac ttc acc atc        872
Asn Ile Tyr Lys Leu Phe Glu Asn Ile Gly Arg Gly Asp Phe Thr Ile
    260                 265                 270 cct tgt gac tgc ggc cca cca ctc tct gac cta ctc cga ggg atg ttg        920
Pro Cys Asp Cys Gly Pro Pro Leu Ser Asp Leu Leu Arg Gly Met Leu
275                 280                 285                 290 gag tat gag ccg gcc aag agg ttc tcc atc cga cag att agg cag cac        968
Glu Tyr Glu Pro Ala Lys Arg Phe Ser Ile Arg Gln Ile Arg Gln His
                295                 300                 305 agc tgg ttc cgg aag aaa cac cct ctg gct gag gcg ctc gta cct atc       1016
Ser Trp Phe Arg Lys Lys His Pro Leu Ala Glu Ala Leu Val Pro Ile
            310                 315                 320 cca cca agc cca gac act aag gac cgc tgg cgc agt atg act gta gtg       1064
Pro Pro Ser Pro Asp Thr Lys Asp Arg Trp Arg Ser Met Thr Val Val
        325                 330                 335 ccc tac ctg gag gac ctg cat ggc cgt gcg gag gag gag gag gag gaa       1112
Pro Tyr Leu Glu Asp Leu His Gly Arg Ala Glu Glu Glu Glu Glu Glu
    340                 345                 350 gac ttg ttt gac att gag gac ggc att atc tac acc cag gac ttc aca       1160
Asp Leu Phe Asp Ile Glu Asp Gly Ile Ile Tyr Thr Gln Asp Phe Thr
355                 360                 365                 370 gtg cct gga cag gtc ctg gaa gag gaa gtg ggt cag aat gga cag agc       1208
Val Pro Gly Gln Val Leu Glu Glu Glu Val Gly Gln Asn Gly Gln Ser
                375                 380                 385 cac agt ttg ccc aag gct gtt tgt gtg aat ggc aca gag ccc cag ctc       1256
His Ser Leu Pro Lys Ala Val Cys Val Asn Gly Thr Glu Pro Gln Leu
            390                 395                 400 agc agc aag gtg aag cca gaa ggc cga cct ggc acc gcc aac cct gcg       1304
Ser Ser Lys Val Lys Pro Glu Gly Arg Pro Gly Thr Ala Asn Pro Ala
        405                 410                 415 cgc aag gtg tgc tcc agc aac aag atc cgc cgg ctc tcg gcc tgc aag       1352
Arg Lys Val Cys Ser Ser Asn Lys Ile Arg Arg Leu Ser Ala Cys Lys
    420                 425                 430
```

-continued

```
cag cag tgactgaggc ctacagtgtg tcatcaggat ctctgggcag gtgtccctgc      1408
Gln Gln
435 aaggctgggt tttccaggcc tgcctgtcca ctcacttcgg gacgttggag ccgagggcgg   1468 acctgctgcc ccagaagcac tttatgtcga gaccactggc cggccttgcc tgcatgccgc   1528 cctgcgagcc tcgctgtctt tgggttggtt tcttttttt taataaaaca ggtggatttg    1588 agctatggct atgagggtgt ttggaaatat ggagcaggcg gggcacaggg tggcctgcag   1648 agaaaaccag agcaaacaaa tatgcagaga catttatgat taaccagaca acacgaccaa   1708 ccacagaggg cgcagggcag ggagtgggca ggcactcaca gcgagtctgc cctatctttt   1768 ggcaataaat aaagctttggg aaacttg                                     1795

<210> SEQ ID NO 2
<211> LENGTH: 436
<212> TYPE: PRT
<213> ORGANISM: Mus musculus

<400> SEQUENCE: 2

Met Asp Val Ala Asp Pro Glu Pro Leu Gly Leu Phe Ser Gly Glu
  1               5                  10                  15

Leu Met Ser Val Gly Met Asp Thr Phe Ile His Arg Ile Asp Ser Thr
             20                  25                  30

Glu Val Ile Tyr Gln Pro Arg Arg Lys Arg Ala Lys Leu Ile Gly Lys
         35                  40                  45

Tyr Leu Met Gly Asp Leu Leu Gly Glu Gly Ser Tyr Gly Lys Val Lys
     50                  55                  60

Glu Val Leu Asp Ser Glu Thr Leu Cys Arg Arg Ala Val Lys Ile Leu
 65                  70                  75                  80

Lys Lys Lys Lys Leu Arg Arg Ile Pro Asn Gly Glu Ala Asn Val Lys
                 85                  90                  95

Lys Glu Ile Gln Leu Leu Arg Arg Leu Arg His Arg Asn Val Ile Gln
            100                 105                 110

Leu Val Asp Val Leu Tyr Asn Glu Glu Lys Gln Lys Met Tyr Met Val
        115                 120                 125

Met Glu Tyr Cys Val Cys Gly Met Gln Glu Met Leu Asp Ser Val Pro
    130                 135                 140

Glu Lys Arg Phe Pro Val Cys Gln Ala His Gly Tyr Phe Arg Gln Leu
145                 150                 155                 160

Ile Asp Gly Leu Glu Tyr Leu His Ser Gln Gly Ile Val His Lys Asp
                165                 170                 175

Ile Lys Pro Gly Asn Leu Leu Leu Thr Thr Asn Gly Thr Leu Lys Ile
            180                 185                 190

Ser Asp Leu Gly Val Ala Glu Ala Leu His Pro Phe Ala Val Asp Asp
        195                 200                 205

Thr Cys Arg Thr Ser Gln Gly Ser Pro Ala Phe Gln Pro Pro Glu Ile
    210                 215                 220

Ala Asn Gly Leu Asp Thr Phe Ser Gly Phe Lys Val Asp Ile Trp Ser
225                 230                 235                 240

Ala Gly Val Thr Leu Tyr Asn Ile Thr Thr Gly Leu Tyr Pro Phe Glu
                245                 250                 255

Gly Asp Asn Ile Tyr Lys Leu Phe Glu Asn Ile Gly Arg Gly Asp Phe
            260                 265                 270

Thr Ile Pro Cys Asp Cys Gly Pro Pro Leu Ser Asp Leu Leu Arg Gly
        275                 280                 285
```

```
Met Leu Glu Tyr Glu Pro Ala Lys Arg Phe Ser Ile Arg Gln Ile Arg
    290                 295                 300
Gln His Ser Trp Phe Arg Lys Lys His Pro Leu Ala Glu Ala Leu Val
305                 310                 315                 320
Pro Ile Pro Pro Ser Pro Asp Thr Lys Asp Arg Trp Arg Ser Met Thr
                325                 330                 335
Val Val Pro Tyr Leu Glu Asp Leu His Gly Arg Ala Glu Glu Glu
            340                 345                 350
Glu Glu Asp Leu Phe Asp Ile Glu Asp Gly Ile Ile Tyr Thr Gln Asp
        355                 360                 365
Phe Thr Val Pro Gly Gln Val Leu Glu Glu Val Gly Gln Asn Gly
    370                 375                 380
Gln Ser His Ser Leu Pro Lys Ala Val Cys Val Asn Gly Thr Glu Pro
385                 390                 395                 400
Gln Leu Ser Ser Lys Val Lys Pro Glu Gly Arg Pro Gly Thr Ala Asn
                405                 410                 415
Pro Ala Arg Lys Val Cys Ser Ser Asn Lys Ile Arg Arg Leu Ser Ala
                420                 425                 430
Cys Lys Gln Gln
        435

<210> SEQ ID NO 3
<211> LENGTH: 5876
<212> TYPE: DNA
<213> ORGANISM: Mus musculus
<220> FEATURE:
<221> NAME/KEY: exon
<222> LOCATION: (1)...(84)
<220> FEATURE:
<221> NAME/KEY: intron
<222> LOCATION: (85)...(677)
<220> FEATURE:
<221> NAME/KEY: exon
<222> LOCATION: (678)...(767)
<220> FEATURE:
<221> NAME/KEY: intron
<222> LOCATION: (768)...(1231)
<220> FEATURE:
<221> NAME/KEY: exon
<222> LOCATION: (1232)...(1364)
<220> FEATURE:
<221> NAME/KEY: intron
<222> LOCATION: (1365)...(1431)
<220> FEATURE:
<221> NAME/KEY: exon
<222> LOCATION: (1432)...(1568)
<220> FEATURE:
<221> NAME/KEY: intron
<222> LOCATION: (1569)...(1852)
<220> FEATURE:
<221> NAME/KEY: exon
<222> LOCATION: (1853)...(1980)
<220> FEATURE:
<221> NAME/KEY: intron
<222> LOCATION: (1981)...(2243)
<220> FEATURE:
<221> NAME/KEY: exon
<222> LOCATION: (2244)...(2301)
<220> FEATURE:
<221> NAME/KEY: intron
<222> LOCATION: (2302)...(3102)
<220> FEATURE:
<221> NAME/KEY: exon
<222> LOCATION: (3103)...(3299)
<220> FEATURE:
<221> NAME/KEY: intron
<222> LOCATION: (3300)...(5103)
<220> FEATURE:
```

```
<221> NAME/KEY: exon
<222> LOCATION: (5104)...(5310)
<220> FEATURE:
<221> NAME/KEY: intron
<222> LOCATION: (5311)...(5454)
<220> FEATURE:
<221> NAME/KEY: exon
<222> LOCATION: (5455)...(5876)

<400> SEQUENCE: 3
ggagatccag ctgctgcggc ggctgcggca tcggaatgtg atccagcttg tggacgtgct      60
gtacaatgag gagaagcaga agatatatcc tgtgggtgga gtgggctggg gtggcccctg     120
tgttaggggc tggaagcctt ctgcaaggcc tctggcagca atagtgctac atgtcatcct     180
gtggtgcctg tcagctcatc aggcagggga gcaaggcatg gggcttccac ctggtgccag     240
cctgttctga gcagtgtggc tgggactggg catggcctca cagggacttg gggcctatgt     300
acattgacag ggccccggct ggttctagag gtttccatgc tgcccctttcc cagaggtaga    360 ggttgcacag cctacgttgc atctgggcag tcctgggagc attctgagaa cccagtgccc     420
tgcagcccca actcctggta cccatctctc cctgtggcta gtacaccagc tgatttcagt     480
cctgttgtaa tctatgctga ctccatgtgg tccaagtcac tgtggtggtc ttgtggaccc     540
tgtgagtact gatagggagc gcagaatggc gggagagcag agtggtggtg gtctgttggc     600 ccagcgggc cctccagacc actgttgcta ggagcagggc tcctgggctt ggtgtgctgc      660
tttccttagc gccctacgta tatggtgatg gagtactgcg tatgtggcat gcaggagatg     720
ctggacagtg tgccggagaa gcgcttccct gtgtgccaag ctcatgggtg agtgccctgc    780
tgggtgcagg aggagcagcc attgtcagga acccaggtg tttctgggcc cccagttttt     840
aacccagcca atgtgcttag ggttaccctc ttgttaggcc ctgtggtccc gctgccctgc   900
agagccatag tgggtctgag tcctgttcag tgctcccagg ttcagcagaa tcacatcccc  960
tggttagcag agaacaaagg gaagggaagg gaaggaagca agccagaggg gaaacctggc  1020
tccctgggcc tgggcagcag tgactgccag ttgccctgtg taattttagt ggcccagcct  1080
tctgactctc aggtctgttt gcctgagccc taaacatcta tcaccttgta ggccaggtct  1140
catgagtctc ccaaacttca tatcagactt atgtaggtac catggtatgg gctgagacac  1200 tgtgggcct gagccagtcc cacccattca ggtacttccg ccagctgatt gacggcctgg   1260
aatacctaca cagccagggc attgttcaca aggacatcaa gccgggcaac ctgctactca  1320
ccaccaatgg cacactcaag atctccgacc tcggtgttgc cgaggtaggc accatgtgca  1380
gggatcatgg gccgcttctc ctgagctgcc ctgactctca ctgccctgca ggccctgcac  1440
cctttcgctg tggatgacac ctgccggaca agccagggct ccccggcctt ccagcctcct  1500
gagattgcca atggactgga cacctttttca ggtttcaagg tggacatctg gtcagctggg  1560
gtcacactgt aagtgtcttg tgtgtaccct gtagcagatg gggggctgtg ggttttccct  1620
agtgttcttg ggcctttttg cccacagtgt gtggctagca ggttggacat ccaggtctg   1680 tgggtgtggt tcctcaccct accccacccc actccacagg gttttgcttg cacacagatg  1740
taggtgccat gactgcacat ctaccagtta acatgtgtcc tgtctgggag ttggggcacc  1800
tgtcctctgg tctccagtgt ggccagcact gacactcttt tcctatgtga agttacaaca  1860
tcaccacggg cctgtaccca tttgagggg acaatatcta caagctcttt gagaacattg   1920
ggagaggaga cttcaccatc ccttgtgact gcggccccac actctctgac ctactccgag  1980
gtgggcatct ctaaatcacc caaatgttag gacagcaagg gacagagccc ctggtctgga  2040
```

-continued

```
ggggttctga ccttactgtc aggacagcct ttgtccgcca ggatgggagg tttctgagat    2100
tgcttccccc catctggggc cggggtgggt ggtgggggtc tcagtgctat ggggcctagg    2160
aaggccaagg ggatggatgc tgtagtggtg ctgtagcaca aagcaggcac ctgctacact    2220
cacttatctc ttctgtccta cagggatgtt ggagtatgag ccggccaaga ggttctccat    2280
ccgacagatt aggcagcaca ggtgagcatg gccggcctgt ctcagcctgc tgggggtctg    2340
agctgagaac atggtctcag aggtgctagg tcatcacagg agtaaggatc agtgtgctgt    2400
gtgtattgat gtctgggaag gctgtgtgtg aacttggggt gtgacagggg tgcccaatgc    2460
aggcctccct acctttatca ttttgttcag gagtgcaggc gttatgtggc ctgagaagct    2520
gtagatttca gggcctagaa ttagagacgg atcctcccat ggtggggagg gaggagtaga    2580
tggggaagtg tcactttgga tcccagctgt tccttggcca tctggacatg gaaatgtgtc    2640
tagggaggcc aacaggaagc gtgaggcatg gtgtctttcc tcacctgagg ctaagagcct    2700
tctgggtaac agtggagcct ctgtcctccc tttgtttatt taccagctgg tcagagcctt    2760
tgggtccagg cttctctgtc ctcttctccc ttcatgctag actgagactg gctcagctgg    2820
gtgtccccca gtgagggctt ctagcctatc cgtgttcaag gcgggtggga ctataggtgc    2880
agggacctga ttgcccaccc tagtccaagg cgctgtggct gtcatcagtg ggtggtggtt    2940
tgtgccagtg ctatgggtgt taggctacct caagcctgta gccggagcac taaggcctcg    3000
tcttatgtaa ggacagccat ggtgtgggct ttggtgggta ttggccagcc gtggtcacag    3060
tgcctggcac ctgatgtctg tgctgcactt ggccttcttt agctggttcc ggaagaaaca    3120
ccctctggct gaggcgctcg tacctatccc accaagccca gacactaagg accgctggcg    3180
cagtatgact gtagtgccct acctggagga cctgcatggc cgtgcggagg aggaggagga    3240
ggaagacttg tttgacattg aggacggcat tatctacacc caggacttca cagtgcctgg    3300
taagctggct tggcgcagct cctactggag ctggtgactt tgtgcactct ggggctggtc    3360
cccttcccaa gtctccagcc agctaacatg agccaccagg actgccaaag ccatcctggt    3420
ggctgtggca tttcactctg ggctagatga agggctccct ggctgcatct agcaggagga    3480
ggggaaccct ggagggcagt gggtaggggc cctgagacag ccacctgagg gagggtccag    3540
tggccctcgg tcctgccat gcctgaccct atatcgcctt cttccccagg tgtcgaggag    3600
gcggccgagg cagggcttag cgaggatgca tgcgacacat gcatgtggaa gagccagggc    3660
gcaggccttc ctggagagga gcccgaggag gggtttgggg ctttagtgta gctccctgtc    3720
tgctgcccca cccatgtcct ccataaagct ttgtccactg tgtctgcagg tggatgcttg    3780
ccgcgacttc cctcctgtca ctaccctgac aggctcccca ccagggtttc agagaacatg    3840
cctgggtcca aggcctgagc taggtcctca gtgccagggt ggccaccagc cagggctct    3900 tggggccttt gttcctgtgg cctgcatgcc agtcccactt agctcctggc ctttcaaata    3960
gctttggtgg gagggtaagg accttgggct actgtgtctc ctgtagcaat tgagagttct    4020
aatagcagtg cccgctgggt gccaggtgga atccacaagg acaggtatac acctgatgtc    4080
cagtatgggc cttggccaca gccctttcta aggtttaaag catccctatg tgggaatagt    4140
gtcttctact ctgtcacgtg gagcccttgt ctagactgtc ccacaggctg ggctcctggc    4200
tgagagctgt tttctctgct ggggagaaga tgtacttagg tgctggttgc atgagggacc    4260
cttaaggctg ctgtggtttg aaggaaggca agggtctggg gacactggtt ggccatggag    4320
cccatttgtc aaatggggta gtgttgcaca gagtgaagtg accgtgctct gaggatagcc    4380
tgatccctct gtacttggca tgagggtcgg actctgcagc aacaggacag gggctttcta    4440
```

-continued

```
ctcagtgcct tgtgtggagg agggaacaga tgctttctca gagtccacct gacctcaagc    4500
ctcagtccca tgcagagtga gccagagtgg gtgctgctag tgtggccaag tcagagggtt    4560
tgggagagaa attctggatc caggagcgtg ggcagtgggc tgtgtgctgg gttccacagc    4620
cgcattgcca agcactggac tgtggagtta catgtagaca ctgacctctg gagcctggga    4680
agcttcagga gaggccatct tttgtcccac tgcgagggca ggccaacaga gcaagctggt    4740
ctgcagccct cagctggatg atctccttcc cggtgctcat cgcagctagt agctcccagg    4800
ccgaatgctt catctccttg tgcctgtact gagggtctag agcctctccc ttggagagct    4860
ctgtgagctg gtgctgggct gcccaggcta gacaggcagg tgagcgtggg catgctgcag    4920
gagggccagg gcatagcact gtgaaggcag tgggcctgct tgcctttgga gctactgagg    4980
ggtgggtggc accagaggct agagcacctc cgaccagcct ctgtcacagt tgggctggc    5040 tgggccctgg ggctttgagc tacctgcccc ttggctcaag ctatgcttgc catcttcccg    5100
taggacaggt cctggaagag gaagtgggtc agaatggaca gagccacagt ttgcccaagg    5160
ctgtttgtgt gaatggcaca gagccccagc tcagcagcaa ggtgaagcca gaaggccgac    5220
ctggcaccgc caaccctgcg cgcaaggtgt gctccagcaa caagatccgc cggctctcgg    5280
cctgcaagca gcagtgactg aggcctacag gtgggcatgg gcctgggtcc agccatccct    5340
ggtgttcaca gtgggtgtct gctgggctcc tagctccttc ccgtagggca gtgctgcaag    5400
ggggaaggtc tggtggttga ggtggtacta agtgaccacc cattctacca acagtgtgtc    5460
atcaggatct ctgggcaggt gtccctgcaa ggctgggttt tccaggcctg cctgtccact    5520
cacttcggga cgttggagcc gagggcggac ctgctgcccc agaagcactt tatgtcgaga    5580
ccactggccg gccttgcctg catgccgccc tgcgagcctc gctgtctttg ggttggtttc    5640
ttttttttta ataaaacagg tggatttgag ctatggctat gagggtgttt ggaaatatgg    5700
agcaggcggg gcacagggtg gcctgcagag aaaacccaga gcaaacaaat atgcagagac    5760
atttatgatt aaccagacaa cacgaccaac cacagagggc gcagggcagg gagtgggcag    5820
gcactcacag cgagtctgcc ctatctttg gcaataaata aagcttggga aacttg          5876
```

<210> SEQ ID NO 4
<211> LENGTH: 33
<212> TYPE: DNA
<213> ORGANISM: Artificial Sequence
<220> FEATURE:
<223> OTHER INFORMATION: Artificially Synthesized Primer Sequence

<400> SEQUENCE: 4
gatgaattcc gaaggacaga ggacaaagag tgg                                  33

<210> SEQ ID NO 5
<211> LENGTH: 60
<212> TYPE: DNA
<213> ORGANISM: Artificial Sequence
<220> FEATURE:
<223> OTHER INFORMATION: Artificially Synthesized Primer Sequence

<400> SEQUENCE: 5
gatgaattct tagaggtctt cttctgagat gagcttctgc tcctgctgct tgcaggccga    60

<210> SEQ ID NO 6
<211> LENGTH: 24
<212> TYPE: DNA
<213> ORGANISM: Artificial Sequence
<220> FEATURE:

-continued

<223> OTHER INFORMATION: Artificially Synthesized Primer Sequence

<400> SEQUENCE: 6
tgcgcagctt tttcttcttg agga    24

<210> SEQ ID NO 7
<211> LENGTH: 21
<212> TYPE: DNA
<213> ORGANISM: Artificial Sequence
<220> FEATURE:
<223> OTHER INFORMATION: Artificially Synthesized Primer Sequence

<400> SEQUENCE: 7
ggtgatggag tactgcgtgt g    21

<210> SEQ ID NO 8
<211> LENGTH: 24
<212> TYPE: DNA
<213> ORGANISM: Artificial Sequence
<220> FEATURE:
<223> OTHER INFORMATION: Artificially Synthesized Primer Sequence

<400> SEQUENCE: 8
ggtgaagtct cctctcccaa tgtt    24

<210> SEQ ID NO 9
<211> LENGTH: 24
<212> TYPE: DNA
<213> ORGANISM: Artificial Sequence
<220> FEATURE:
<223> OTHER INFORMATION: Artificially Synthesized Primer Sequence

<400> SEQUENCE: 9
actgcagctg acccaagcca ggat    24

<210> SEQ ID NO 10
<211> LENGTH: 24
<212> TYPE: DNA
<213> ORGANISM: Artificial Sequence
<220> FEATURE:
<223> OTHER INFORMATION: Artificially Synthesized Primer Sequence

<400> SEQUENCE: 10
cgaaggacag aggacaaaga gtgg    24

<210> SEQ ID NO 11
<211> LENGTH: 27
<212> TYPE: DNA
<213> ORGANISM: Artificial Sequence
<220> FEATURE:
<223> OTHER INFORMATION: Artificially Synthesized Linker Sequence

<400> SEQUENCE: 11
tgcgacacat cgataccgct cgagtcg    27

<210> SEQ ID NO 12
<211> LENGTH: 35
<212> TYPE: DNA
<213> ORGANISM: Artificial Sequence
<220> FEATURE:
<223> OTHER INFORMATION: Artificially Synthesized Linker Sequence

<400> SEQUENCE: 12
aattcgactc gagcggtatc gatgtgtcgc atgca    35

```
<210> SEQ ID NO 13
<211> LENGTH: 109
<212> TYPE: DNA
<213> ORGANISM: Artificial Sequence
<220> FEATURE:
<223> OTHER INFORMATION: Artificially Synthesized Linker Sequence

<400> SEQUENCE: 13
ctagtcaagc ttcataactt cgtatagcat acattatacg aagttatcga attcgacctg     60
gatcccataa cttcgtatag catacattat acgaagttat caagcttcc                109

<210> SEQ ID NO 14
<211> LENGTH: 109
<212> TYPE: DNA
<213> ORGANISM: Artificial Sequence
<220> FEATURE:
<223> OTHER INFORMATION: Artificially Synthesized Linker Sequence

<400> SEQUENCE: 14
tcgaggaagc ttgataactt cgtataatgt atgctatacg aagttatggg atccaggtcg     60
aattcgataa cttcgtataa tgtatgctat acgaagttat gaagcttga                109

<210> SEQ ID NO 15
<211> LENGTH: 36
<212> TYPE: DNA
<213> ORGANISM: Artificial Sequence
<220> FEATURE:
<223> OTHER INFORMATION: Artificially Synthesized Linker Sequence

<400> SEQUENCE: 15
gatgttccac ctcgagccca ggctccagag gtcagt                               36

<210> SEQ ID NO 16
<211> LENGTH: 86
<212> TYPE: DNA
<213> ORGANISM: Artificial Sequence
<220> FEATURE:
<223> OTHER INFORMATION: Artificially Synthesized Primer Sequence

<400> SEQUENCE: 16
gatctcgaga tcgatggtac cggtgttcca cataacttcg tatagcatac attatacgaa     60
gttatctgtc cactgtgtct gcaggt                                          86

<210> SEQ ID NO 17
<211> LENGTH: 20
<212> TYPE: DNA
<213> ORGANISM: Artificial Sequence
<220> FEATURE:
<223> OTHER INFORMATION: Artificially Synthesized Primer Sequence

<400> SEQUENCE: 17
ccggtgttcc acataacttc                                                 20

<210> SEQ ID NO 18
<211> LENGTH: 24
<212> TYPE: DNA
<213> ORGANISM: Artificial Sequence
<220> FEATURE:
<223> OTHER INFORMATION: Artificially Synthesized Primer Sequence

<400> SEQUENCE: 18
gtttcccaag ctttatttat tgcc                                            24

<210> SEQ ID NO 19
```

```
<211> LENGTH: 24
<212> TYPE: DNA
<213> ORGANISM: Artificial Sequence
<220> FEATURE:
<223> OTHER INFORMATION: Artificially Synthesized Primer Sequence

<400> SEQUENCE: 19
cagcagcaag gtgaagccag aagg                                              24

<210> SEQ ID NO 20
<211> LENGTH: 24
<212> TYPE: DNA
<213> ORGANISM: Artificial Sequence
<220> FEATURE:
<223> OTHER INFORMATION: Artificially Synthesized Primer Sequence

<400> SEQUENCE: 20
cctttggctg ctgggtgact tctg                                              24

<210> SEQ ID NO 21
<211> LENGTH: 20
<212> TYPE: DNA
<213> ORGANISM: Artificial Sequence
<220> FEATURE:
<223> OTHER INFORMATION: Artificially Synthesized Primer Sequence

<400> SEQUENCE: 21
acagagctct ccaagggaga                                                   20

<210> SEQ ID NO 22
<211> LENGTH: 20
<212> TYPE: DNA
<213> ORGANISM: Artificial Sequence
<220> FEATURE:
<223> OTHER INFORMATION: Artificially Synthesized Primer Sequence

<400> SEQUENCE: 22
ctctcccaaa ccctctgact                                                   20
```

LKB1 GENE KNOCKOUT MICE

This application is a continuation-in-part of PCT/JP00/03504, filed May 31, 2000, which claims priority to Japanese Patent Application No. 11/153030, filed May 31, 1999.

TECHNICAL FIELD

The present invention relates to mammals engineered to have a functional deficiency in the LKB1 gene as well as to a preparation method thereof. The human LKB1 gene is a causative gene of Peutz-Jeghers syndrome, and thus such mammals can be used to develop methods to treat the disease and therapeutic agents therefor.

BACKGROUND

Peutz-Jeghers syndrome (MIM 175200, PJS) is a human genetic disease the major go symptoms of which include polyposis in the digestive tract and pigmental spot formation on mucous membranes and skin. PJS is inherited in an autosomal-dominant fashion. In 1997, Hemminki et al. reported that the causative gene for the disease was mapped on p13.3 region of chromosome 19 based on the linkage analysis of PJS patient families (Hemminki et al., Nat. Genet. 15:87–90, 1997). There exists the novel serine/threonine kinase, LKB1, which was found by the present inventors in this region. Based on the fact, Jenne et al. predicted that this gene is a candidate for the causative gene and carried out mutational analysis of the LKB1 (STK11) gene in PJS patients. Their results showed that all the patients tested had mutations in the LKB1 gene (PCT/JP98-05357; Jenne et al., Nat. Genet. 18:38–43, 1998). In addition, other groups also reported similar results, one after another. More than 60 types of mutations in the LKB1 gene have been found to date in PJS patients (Hemminki et al., Nature 391:184–7, 1998; Nakagawa et al., Hum. Genet. 103:168–72, 1998; Resta et al., Cancer Res. 58:4799–801, 1998; Ylikorkala et al., Hum. Mol. Genet. 8:45–51, 1999).

Further, the present inventors have demonstrated that the product of the LKB1 gene is a kinase having the ability of autophosphorylation, and that missense mutations that have been found in PJS patients result in loss of the kinase activity (Mehenni et al., Am. J. Hum. Genet. 63:1641–50, 1998).

Based on these findings, it has been clarified that functional deficiency of the LKB1 serine/threonine kinase due to gene mutations is the cause of PJS.

Further, epidemiological studies have shown that PJS patients have markedly increased risks for the onset of a variety of cancers compared with healthy normal persons. Thus, it has been suggested that the PJS causative gene should have a tumor suppressor gene like activity. In fact, it has been reported that mutations are found in the LKB1 gene in some sporadic cancers unrelated to PJS. Therefore, it has been elucidated that functional inactivation of the LKB1 gene is related to general sporadic cancers (Dong et al., Cancer Res. 58:3787–90, 1998; Rowan et al., J. Invest. Dermatol. 112:509–11, 1999; Guldberg et al., Oncogene 18:1777–80, 1999). However, specific physiological functions of LKB1 in normal cells as well as the mechanism for polyposis or cancerization induced by its functional inactivation has remained obscure.

SUMMARY

This situation led to the present invention, and the object of the present invention is to provide non-human mammals useful for analyzing LKB1 functions and for developing agents to treat diseases caused by LKB1 mutations. More specifically, the object of the invention is to provide knockout animals, in which the expression of the LKB1 gene is artificially suppressed, as well as to provide methods for preparing the animals. In a preferred embodiment, the present invention provides non-human mammals in which deletion of the endogenous LKB1 is achieved in an inducible manner.

The present inventors created mammal models, in which the LKB1 gene is artificially deleted, or in which the deletion can be induced. Specifically, as shown in the Examples, a mouse LKB1 gene (both the genomic DNA and cDNA) was cloned; a vector for homologous recombination was constructed using the cloned gene; the vector was introduced into mouse embryonic stem cells (ES cells) to obtain recombinant clones; and the clone was introduced back to an individual mouse which then enabled acquisition of mice having mutations in the LKB1 gene. The present inventors used Cre-loxP system (described later) in creating the recombinant mouse, and thus, achieved phase-specific and tissue-specific induction of mutations in the LKB1 gene. According to this method, the inventors overcame the previous problem of potential embryonic lethality caused by the inactivation of the gene of interest. The mammals in accordance with the present invention (and cell lines established thereof) are expected to be useful as tools to study the onset mechanism of a variety of diseases caused by LKB1 gene deficiency, such as PJS and cancers, and furthermore, are highly useful tools in the development of therapeutic methods and agents for these diseases. Thus, these mammals and cells are expected to be used for various purposes.

The present invention relates to non-human mammals, in which the expression of the LKB1 gene can be or is artificially suppressed, as well as methods for creating the same. More specifically, the present invention relates to the following:

(1) a non-human mammal in which the expression of the endogenous LKB1 gene can be artificially suppressed;

(2) the non-human mammal of (1), wherein the suppression of the expression of the endogenous LKB1 gene is induced by deleting at least a part of the gene or the regulatory region thereof;

(3) the non-human mammal of (1) or (2), wherein at least a part of the LKB1 gene or the regulatory region thereof in the genome is inserted between at least a pair of loxP sequences;

(4) the non-human mammal of any of (1) to (3), wherein the mammal is a rodent;

(5) the non-human mammal of (4), wherein the rodent is a mouse;

(6) a non-human mammal wherein the expression of the endogenous gene encoding LKB1 is artificially suppressed;

(7) the non-human mammal of (6), wherein the expression of the endogenous gene encoding LKB1 is suppressed by a defect in at least a part of the gene or the regulatory region thereof;

(8) the non-human mammal of (6) or (7), wherein the mammal is a rodent;

(9) the non-human mammal of (8), wherein the rodent is a mouse;

(10) a non-human mammalian cell wherein the suppression of the expression of the endogenous gene encoding LKB1 can be artificially induced, further wherein the cell can be differentiated or developed into an individual mammal;

(11) the non-human mammalian cell of (10), wherein the suppression of the expression of the endogenous gene encoding LKB1 is induced by deleting at least a part of the gene or the regulatory region thereof;

(12) the non-human mammalian cell of (10) or (11), wherein at least a part of the LKB1 gene or the regulatory region thereof in the genome is inserted between at least a pair of loxP sequences;

(13) the non-human mammalian cell of (12), wherein the cell contains the Cre gene in an expressible manner;

(14) the non-human mammalian cell of any of (10) to (13), wherein the cell is a rodent cell;

(15) the non-human mammalian cell of (14), wherein the cell is a mouse cell;

(16) the non-human mammalian cell of any of (10) to (15), wherein the cell is an embryonic stem cell;

(17) a non-human mammalian cell, wherein the expression of the endogenous gene encoding LKB1 is artificially suppressed, further wherein the cell can be differentiated or developed into an individual mammal;

(18) the non-human mammalian cell of (17), wherein the expression of the endogenous gene encoding LKB1 is suppressed by a defect in at least a part of the gene or the regulatory region thereof;

(19) the non-human mammalian cell of (18), wherein the cell can be obtained by expressing the Cre gene in the non-human mammalian cell described in (12);

(20) the non-human mammalian cell of any of (17) to (19), wherein the cell is a rodent cell;

(21) the non-human mammalian cell of (20), wherein the cell is a mouse cell;

(22) the non-human mammalian cell of any of (17) to (21), wherein the cell is an embryonic stem cell;

(23) a method for creating the non-human mammal described in any of (1) to (5), which comprises the following steps:
 (a) introducing the non-human mammalian cell described in (16) into an embryo obtained from a pregnant female; and
 (b) transplanting the embryo into the uterus of a pseudopregnant female;

(24) a method for creating the non-human mammal described in any of (6) to (9), which comprises the following steps:
 (a) introducing the non-human mammalian cell described in (22) into an embryo obtained from a pregnant female; and
 (b) transplanting the embryo into the uterus of a pseudopregnant female;

(25) a method for creating the non-human mammal described in (7), which comprises the following steps:
 (a) providing a fertilized egg or embryo from the non-human mammal described in (3);
 (b) expressing the Cre gene in the fertilized egg or embryo after introduction of the gene; and
 (c) transplanting the fertilized egg or embryo into the uterus of a pseudopregnant female;

(26) a method for creating the non-human mammal described in (7), which comprises the step to introducing the Cre gene into the non-human mammal described in (3) and expressing the gene; and

(27) a method for creating the non-human mammal described in (7), which comprises the step of mating the non-human mammal described in (3) with a non-human mammal containing a Cre gene in its genome and obtaining their offspring.

According to the present invention, "suppression of the gene expression" includes complete suppression and partial suppression, as well as suppression under specific conditions and also suppression of the expression of either one of the two alleles.

Construction of a Vector for Homologous Recombination (Knockout)

In order to create a knockout animal in which the expression of the LKB1 gene is artificially suppressed, first the LKB1 gene is cloned and then a vector for homologous recombination is constructed by using the gene to inactivate the endogenous LKB1 gene in the target animal.

The vector for homologous recombination contains a nucleic acid sequence designed to inactivate the endogenous LKB1 gene in the target animal. Such a nucleic acid sequence can be, for example, a nucleic acid sequence of the LKB1 gene or the regulatory region thereof containing at least a partial deletion, or alternatively it can be a nucleic acid sequence of the LKB1 gene or the regulatory region thereof containing other genes. A gene which can also function as a marker is preferably selected as the gene to be inserted into the LKB1 gene or the regulatory region thereof. The insert genes to be used include, for example, drug-resistance genes, such as the neomycin-resistance gene (selected by G418 resistance), the thymidine kinase gene (selected by ganciclovir), etc.; toxin genes, such as the diphteria toxin (DT) A gene, etc.; or combinations of these genes. There is no particular limitation on the position where the genes may be inserted in the LKB1 gene, so long as the insertion at that position results in the suppression of the expression of the endogenous LKB1 gene in the target.

Alternatively, the nucleic acid sequence may comprise introns of the LKB1 gene in which the loxP (locus of X-ing-over)sequence derived from phage DNA is inserted at more than 2 sites.

The loxP sequence is a sequence recognized by Cre recombinase (Causes recombination), a site-specific recombination enzyme (Sternberg et al., J. Mol. Biol. 150:467–486, 1981). The Cre recombinase recognizes dual loxP sequences, and catalyzes a site-specific recombination between these sites which results in the removal of the gene located between the loxP sequences (hereinafter abbreviated as Cre-loxP system). The Cre-loxP system used to direct site-specific DNA recombination in transgenic animals is described in Orban et al. (1992) Proc Natl Acad Sci USA. 89(15):6861–5, the contents of which are incorporated herein by reference in their entirety.

An application example that uses this system is shown in FIG. 5. It is possible to prepare embryonic stem cells (ES cells) of the following two types: (1) the cell containing conventional gene deletion (type 1), and (2) cell having conditional gene deletion (type 2), by constructing a vector having 3 loxP sequences for homologous recombination, then introducing the vector, for example, into ES cells to obtain recombinant cells, and allowing for the transient expression of the Cre recombinase in the resulting ES cells. When a construct with 3 loxP sequences is used, two types of ES cell clones, each having distinct a genotype, can be advantageously prepared from a single type of recombinant ES cell merely by expressing the Cre recombinase. An individual derived from the type-2 ES cell exhibits the wild-type phenotype, but it can be converted to type 1 by expressing the Cre recombinase gene.

Instead of the Cre-loxP system, it is also possible to use the combination of the FRT (Flp recombinase target)

sequence and Flp recombinase from yeast which recognizes the sequence for site-specific recombination.

The insertion of these genes into the cloned LKB1 gene can be carried out in vitro by using conventional DNA recombination techniques (Sambrook et al., Molecular Cloning, Cold Spring Harbor Laboratory Press, 1989).

Transfection of the Cell

The homologous recombination vector constructed as above is introduced into a non-human mammalian cell capable of differentiating (or developing) into an individual mammal (for example, an ES cell) for homologous recombination with the LKB1 gene in the cell. There is no particular limitation on the type of the organism from which the non-human mammalian cell to be used in the present invention is derived, but preferably it is a rodent such as mouse, rat, hamster, rabbit, and so on.

The introduction of the homologous recombination vector into cells can be performed by methods well known to those skilled in the art, for example, the electroporation method. The introduction results in recombination between the cellular LKB1 gene and the corresponding region of the homologous recombination vector in some population of the cells. In this manner, the wild-type gene is substituted with the gene having the genotype constructed in the homologous recombination vector. Thus, it is possible to obtain cells having an LKB1 gene in which a marker gene and/or loxP sequences have been introduced.

When the homologous recombination vector contains a marker gene, cells can be selected according to this marker gene as an index, due to the loss of the LKB1 gene and the acquired marker gene at the same time in cells where desired homologous recombination has taken place. For example, when a drug-resistance gene is used as the marker gene, cells in which the desired homologous recombination has taken place can be selected by culturing the cells in the presence of the drug at a lethal level subsequent to the introduction of vectors, However, when the Cre-loxP system is used, in some cases, the vector for homologous recombination is designed so that the loxP sequence and the marker gene are integrated into the introns, and accordingly, the LKB1 gene is not always inactivated in the cells. In this system, inactivation of the LKB1 gene can be achieved by expressing the Cre recombinase in the cells to remove the region inserted between a pair of loxP sequences.

The Cre recombinase in the cells can be expressed, for example, by methods employing expression vectors such as adenoviral vectors, or alternatively by mating transgenic animals in which the expression of Cre is regulated by a promoter capable of regulating the expression in a tissue-specific or phase-specific manner with mammals having the Cre-loxP system. The first mating of a transgenic animal having regulated Cre expression with another animal having the Cre-loxP system, results in knockout newborns in which only one allele of the LKB1 gene is deleted (heterozygote), but by further mating these animals, knockout animals in which both alleles of the LKB1 gene are deleted can be obtained.

Injection into Embryos and Transplantation of Embryos

When ES cells are used in the present invention, the cells are injected into blastocysts to prepare chimera embryos. Further, the chimera embryos are transferred into the horn of uterus of pseudopregnant mammals to obtain newborns. The blastocysts to be used for the injection can be obtained by perfusing the uterus of a pregnant female. To determine whether or not the ES cell has been incorporated in the developing embryo after the creation of an individual mammal, it is preferable to select the type of blastocyst that gives different external characteristics (for example, fur color) to distinguish the origin of a cell, whether it is derived from the ES cell or blastocyst, in the created animal.

Subsequently, newborns are obtained by mating the resulting chimera animal with an animal of an appropriate strain of the same species. When the germline of the chimera animal is derived from the homologous recombinant ES cell, it is possible to obtain newborns in which the LKB1 gene has been deleted. However, when the Cre-loxP system is used, some of the homologous recombination vectors may be designed to integrate the loxP sequence and the marker gene into an intron. In this case, the LKB1 gene is not always inactivated. In such cases, it is possible to inactivate the LKB1 gene by expressing the Cre recombinase in the somatic cell or germline cell, such as fertilized egg.

When somatic cells other than ES cells are used in the present invention, it is possible to create a knockout animal by using techniques for creating somatic cell cloned animals. Specifically, for example:

1) a cell that contains a gene to which a mutation is introduced through the homologous recombination is established by the same method as that used for ES cells, using cells other than ES cells such as fibroblast cells;

2) an animal carrying the mutated gene is created from this cell by using the method for creating somatic cell cloned animals (Wilmut et al., Nature 385:810–803, 1997; Wakayama et al., Nature 394:369–374, 1998).

3) the resulting animal newborn carrying the mutated gene corresponds to the F1 mouse of the method using the ES cell, and can be used thereafter according to a same manner as the ES cell.

Use of the Knockout Animal

Knockout animals of the present invention are useful for developing therapeutics and methods to treat a variety of diseases caused by functional defects of the LKB1 gene. For example, a test compound is administered to the knockout animals of the present invention, and the influences on polyp formation, carcinogenesis, and pigment macule formation are tested to select compounds exhibiting desired effects.

Furthermore, cells prepared from knockout animals can be used for developing therapeutics or treatment methods. For example, cells are prepared from embryos and such from knockout animals of the present invention, and then a test compound is added to the cells to determine the influence on cell proliferation, ability to form colony in soft agar or the like, focus forming ability, cell motility, and such, and thereby selecting compounds exhibiting the desired effect. The cells may be primary culture cells or established cell lines. The compounds screened are candidates for pharmaceutical agents.

DESCRIPTION OF DRAWINGS

FIG. 2 shows the nucleotide sequence of the mouse LKB1 gene from exon 2 to exon 10 (SEQ ID NO:3). The exon regions are indicated in uppercase letters and intron regions in lowercase letters.

FIG. 3 is a continuation of FIG. 2.

FIG. 4 is a continuation of FIG. 3.

FIG. 6 shows the structures of the F23 synthetic linker and loxP2 synthetic linker [SEQ ID Nos: 11 (upper) and 12 (lower, oriented in the figure as 3' to 5')] and loxP2synthetic linker [SEQ ID Nos: (upper) and 14 lower (lower, oriented in the figure as 3' to 5')].

Figure 1:
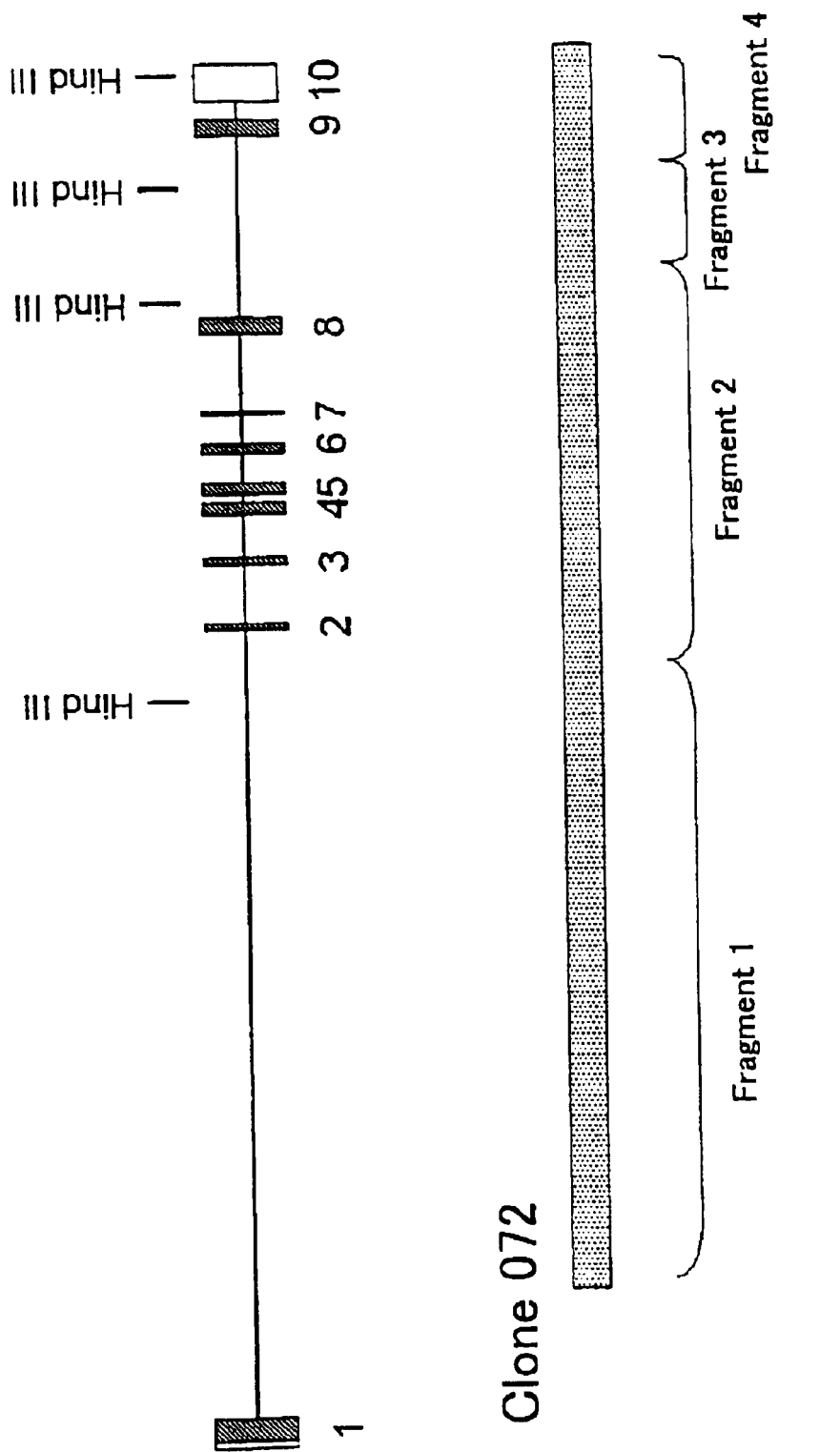
FIG. 1 shows the exon/intron structure of the mouse LKB1 gene. Each exon is indicated by a box. In particular, portions encoding the protein are represented by shaded boxes. The two boxes under the structure indicate the region which is covered by the two cosmid clones, respectively.

Panel B is a photograph showing the result of PCR using the primer set (set B) detecting the null allele. N denotes a sample showing the band (about 1.2 kbp) corresponding to the null allele; O, a sample showing other alleles.

Panel C is a photograph showing the result of Southern blot analysis using probe 7. N denotes a sample showing the band corresponding to the null allele; W, a sample showing only the band derived from the wild-type allele. All the samples show the band derived from the wild-type allele.

DETAILED DESCRIPTION

The present invention is illustrated in detail below with reference to the Examples, but is not to be construed as being limited thereto.

EXAMPLE 1

Preparation of a Homologous Recombination Vector of the LKB1 Gene

In this Example, first the genomic gene of mouse LKB1 was cloned to construct a homologous recombination vector of the mouse LKB1 gene. A homologous recombination vector in which the neomycin-resistance gene and diphteria toxin A gene had been inserted, was constructed to carry out the positive/negative selection using the genomic DNA clone according to the method reported by Yagi et al. (Yagi et al., Analytical Biochemistry 214:77–86, 1993). In this experiment, three loxP sequences in total were inserted, that is, at both ends of the neomycin-resistance gene and also into intron 8 of the LKB1 gene, in the same direction to achieve site-specific homologous recombination mediated by the Cre recombinase. The procedure is specifically described below.

A. Cloning of the Mouse LKB1 Gene

Several mouse-derived ESTs (Expressed Sequence Tag) exhibiting high homology to the human sequence were revealed by searching in the database for the sequence of human LKB1 cDNA. Based on these sequences, MPJ 85 primer (5'-GATGAATTCCGAAGGACAGAGGACAAAGAGTGG-3', SEQ ID NO:4) and LK E2 primer (5'GATGAATTCTTAGAGGTCTTCTTCTGAGATGAGC TTCTGCTCCTGCTGCTTGCAG GCCGA-3', SEQ ID NO:5) were prepared and PCR was carried out using Marathon Ready™ cDNA (CLONTECH) derived from mouse 17-day embryo as the template to amplify the cDNA comprising the entire open reading frame (ORF) of the mouse LKB1. The resulting products were digested at the EcoRI sites attached to both ends of the primers, and then the digest was subcloned into pcDNA3 vector (Invitrogen). The sequence of the gene was determined by sequencing the multiple clones obtained. Further, the 5' end of mouse LKB1 cDNA was cloned by 5' RACE (method for Rapid Amplification of cDNA Ends). Specifically, the fragment of about 400-bp amplified by PCR using mouse 17-day embryo derived Marathon Ready cDNA (CLONTECH) as the template and primers: MPJ15 primer (5'-TGCGCAGCTTTTTCTTCTTGAGGA-3', SEQ ID NO:6) and the adaptor primer (AP1 primer) attached to the kit was subcloned into the pT7Blue-T vector (Novagen) according to the TA cloning method. Several subclones thus obtained were sequenced to determine the 5' end sequence of the mouse LKB1 cDNA. The determined sequence of the mouse LKB1 cDNA is shown in SEQ ID NO:1, and its amino acid sequence in SEQ ID NO:2.

The mouse LKB1 genomic DNA was cloned as follows:

A genomic DNA library of mouse (129/Olastrain) immobilized on a filter was purchased from the German human genome project resource center (RZPD). The library has the following features:

Genomic DNA: DNA prepared from spleen cells of 129/Ola mouse; partially digested with MboI.

Vector: cosmid vector lawrist 7.

The hybridization on this filter, using the human LKB1 cDNA as a probe, and washing of the filter were carried out under a commonly used condition. Accordingly, positive signal for two clones, P2436Q3 (clone 243) and L07209Q3 (clone 072), were detected. These clones were purchased from RZPD and it was confirmed by PCR that they contained the mouse LKB1 gene. Specifically, E. coli containing each of the cosmid clones was cultured in LB medium containing 30 µg/ml kanamycin, and then the cosmid DNA was prepared by alkali-SDS method using the QIAGEN maxi kit (Qiagen). It was verified that a fragment of the mouse LKB1 gene was amplified by the PCR using the cosmid DNA as the template, and DJ666primer (5'-GGTGATGGAGTACTGCGTGTG-3', SEQ ID NO:7) and MPJ18primer (5'-GGTGAAGTCTCCTCTCCCAATGTT-3', SEQ ID NO:8).

The nucleotide sequence of the mouse LKB1 gene was directly sequenced from the gene, amplified as separate fragments by PCR from the cosmid DNA, using primers designed based on the mouse LKB1 cDNA sequence and others. The determined genomic DNA sequence was compared with the cDNA sequence to determine the exon/intron structure. The results showed that each of the two clones contained part of intron 1 to exon 10, and that intron 1 contained in clone 072 was several kbp longer than the other clone (FIG. 1). Subsequently, a fragment containing the remaining part of intron 1 as well as exon 1 was cloned by PCR using MPJ67 primer (5'-ACTGCAGCTGACCCAAGCCAGGAT-3', SEQ ID NO:9), designed to correspond to the sequence within intron 1, MPJ13 primer (5'-CGAAGGACAGAGGACAAAGAGTGG-3', SEQ ID NO:10), designed to correspond to the sequence of the 5' untranslated region (UTR) of mouse LKB1 cDNA, and the mouse genomic DNA as the template. The region from exon 1 to exon 10 of the mouse LKB1 genomic DNA was cloned by the procedure as described above. A schematic figure of the exon/intron structure of the mouse LKB1 gene is shown in FIG. 1. In addition, the nucleotide sequence from exon 2 to exon 10 is indicated in SEQ ID NO:3. FIGS. 2, 3, and 4 also show this nucleotide sequence, in which exons are indicated with uppercase letters and introns with lowercase letters.

B. Construction of a Homologous Recombination Vector

The mouse LKB1 gene contained in clone 072 cosmid DNA was divided into 4 fragments (fragments 1 to 4, FIG. 1) by HindIII digestion, and each fragment was subcloned into a plasmid vector. Specifically, the DNA of cosmid clone 072 was first digested with SfiI, and then, the digested ends were blunted by a method using the TaKaRa DNA blunting kit (TaKaRa). The resulting fragment was further digested with HindIII, and the resulting fragment of about 8 kbp (fragment 1) was inserted into a pBluescript II vector (TOYOBO) at the SmaI/HindIII site to obtain clone MGF-10. The DNA of cosmid clone 072 was also digested with HindIII, and then, each of the resulting fragments, one fragment of about 4kbp (fragment 2) and two fragments of about 1 kbp (fragments 3 and 4), were inserted into pUC18 vector (Pharmacia) at the HindIII site to obtain clone MGG-1 (fragment 2), clone MGD-2 (fragment 3), and clone MGD-3 (fragment 4), respectively.

Vectors for homologous recombination were constructed from these subclones by the following procedure. Fragment 1 digested with NotI/XhoI from clone MGF-10 was first inserted into the NotI/XhoI site of the plasmid containing the diphteria toxin A gene and mRNA-destabilizing sequence (A+T) (DT-A cassette B, Yagi et al., Analytical Biochemistry 214:77–86, 1993) to obtain clone LT1. The synthetic linker F23 (FIG. 6) (the upper sequence, SEQ ID NO:11; the lower sequence, SEQ ID NO:12), was inserted between the AvaIII site of clone MGG-1 and the EcoRI site of the vector to obtain clone LT2. The fragment (fragment 2) digested with HindIII/ClaI from LT2 was inserted into the HindIII/ClaI site of clone LT1 to obtain LT4. The loxP2 synthetic linker (FIG. 6) (the upper sequence, SEQ ID NO:13; the lower sequence: SEQ ID NO:14) was inserted into the SpeI/XhoI site of the pBluescript II vector to prepare clone loxP2. The neomycin-resistance gene (without any polyadenylation signal) was inserted into the EcoRI/BamHI site of this clone, and clone loxP2/neo-, a cassette of the neomycin-resistance gene inserted between two loxP sequences, was obtained. The neomycin-resistance gene was cut out from this clone by HindIII digestion, and then inserted at the HindIII site between fragment 1 and fragment 2 of LT4 (intron 1) to obtain clone LT-5. A fragment containing fragment 3 to which a loxP sequence and XhoI/ClaI/KpnI/Cfr10I site had been added to its 5' side was amplified by PCR using clone MGD-2 as the template, and by using LOXP3 A1 primer (5'-GATGTTCCACCTCGAGCCCAGGCTCCAGAGGTCAGT-3', SEQ ID NO: 15) and LOXP3 S3 primer (5'-GATCTCGAGATCGATGGTACCGGTGTTCCACATAACTTCGTATAGCATACATTATACGAAGTTATCTGTCCACTGTGTCTGCAGGT-3', SEQ ID NO:16). The resulting PCR products were inserted into the XhoI site of the pBluescript II vector to obtain clone LT3. Finally, fragment 3 having the loxP sequence attached to the 5' side was digested from clone LT3 by ClaI and XhoI, and then was inserted into the ClaI/XhoI site of clone LT5 on the 3' side of fragment 2 to obtain the homologous recombination vector LT6.

Figure 7:
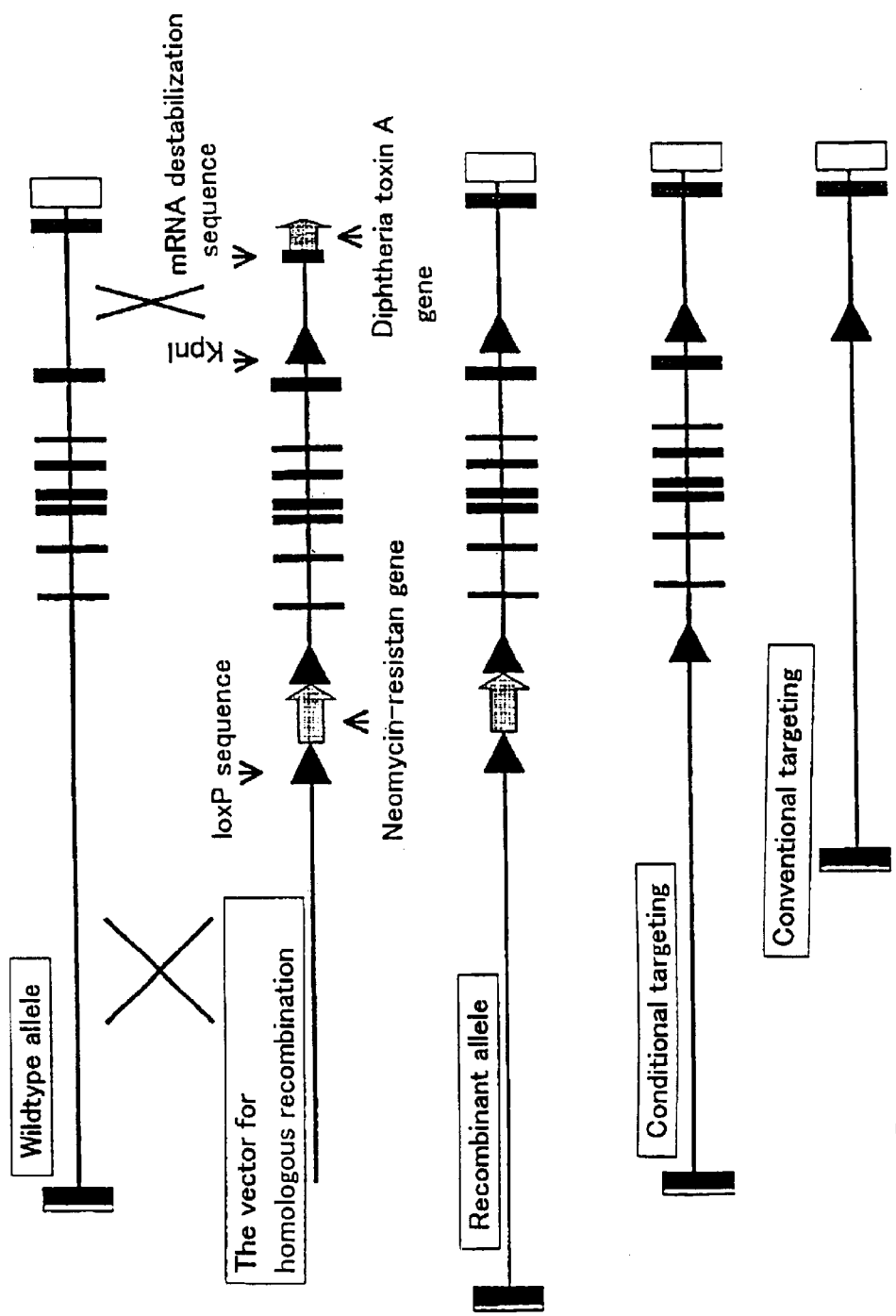
FIG. 7 is a schematic illustration of the homologous recombination vector and the resulting genotype constructed by the introduction of the vector. The recombinant allele is generated by homologous recombination, which occurs in the region marked as X. Two genotypes, conditional targeting and conventional targeting, are generated by the expression of the Cre recombinase.

This vector had the following features (FIG. 7):
(i) the neomycin-resistance gene, having the loxP sequence attached to both ends is inserted in intron 1, and another loxP sequence inserted in intron 8;
(ii) a KpnI site attached to the loxP sequence inserted in intron 8, and therefore, the mutant allele derived from this vector can be identified by Southern blotting;
(iii) the diphteria toxin A gene as a marker gene for negative selection; and
(iv) homologous parts to the wild type LKB1 gene comprising the region of about 7 kb upstream of the neomycin-resistance gene, the region of about 4 kb from the neomycin-resistance gene to the loxP sequence in intron 8, and the region of about 0.9 kb downstream of the loxP sequence in intron 8.

EXAMPLE 2

Establishment of ES cells carrying a mutated LKB1 gene resulting from Homologous Recombination In this Example, the homologous recombination vector was introduced by the electroporation method into mouse ES cells (AB2.2-Prime ES Cells; LEXICON, The Mouse Kit), and subsequently, the cells were selectively cultured in the presence of G418. The resulting G418-resistanct colonies were tested for the recombinants by PCR and Southern blotting. More specifically, the procedure was conducted as follows:

60 μg DNA of the homologous recombination vector (LT6) was digested with NotI to linearize and purify the DNA. The DNA was suspended into a electroporation buffer (LEXICON, The Mouse Kit ESQPBS) containing $3 \times 10^7$ mouse ES cells (AB2.2-Prime ES Cells; LEXICON, The Mouse Kit), and gene introduction was conducted under a condition with a field strength of 575 V/cm and a Capacitance of 500 μF. 24 hours after the introduction, the cells were cultured for selection in a medium containing G418 (Genetisin, Sigma) at a final concentration of 300 μg/ml.

Dulbecco's modified Eagle's culture medium (GIBCO DMEM 11965-092), containing fetal calf serum (FBS) at a final concentration of 15%, L-glutamine (GIBCO 25030-081) at a final concentration of 2 mM, penicillin at a final concentration of 50 U/ml and streptomycin at a final concentration of 50 μg/ml, was used to culture ES cells.

Further, ESQ Feeder cells (LEXICON, The Mouse Kit) were used as feeder cells for ES cell culture; and ESQ DMEM containing FBS at a final concentration of 7% was used as the culture medium. ESQ Feeder cells ($5 \times 10^7$ cells/vial) were rapidly thawed at 37° C. Then the cell count was adjusted to $4.4 \times 10^5$ cells/ml with medium for feeder cells. The resulting cell suspension was dispensed into gelatin-precoated culture dishes (LEXICON, The Mouse Kit ESQ Gelatin); 12 ml/well in 100-mm φdish, 4 ml in 60-mm φdish, 2 ml/well in 6-well plate, 0.5 ml/well in 24-well plate, and in 75 μl/well in 96-well plate. Thus prepared feeder cells were used within 3 weeks.

11 days after the gene was introduced, G418-resistant colonies formed were passaged into wells of 96-well microplate as follows. Specifically, G418-resistant colonies were transferred into a 96-well microplate (Coming 25860MP) containing 30 μl TE solution (Gibco, Trypsin-EDTA 25200-072) by using a micropipette, and was left for several minutes. 70 μl of ES cell culture medium was added to each well, and then the cells were dispersed into single cells by pipetting. The cell suspensions were transferred into wells of a 96-well microplate (Falcon 3072) and then the cells were further cultured. After 3 days, when the cells had grown to confluence in wells of the 96-well microplate, the cells were divided into two batches as follows. Specifically, 25 μl TE was added to disperse the cells, and then the 25 μl ES cell culture medium was added to further disperse the cells into single cells by pipetting. Then, 50 μl of 2×Freezing medium (LEXICON, The Mouse Kit ESQ DMEM:ESQ FBS:DMSO=2:2:1) was added, 20 μl thereof was passaged to a gelatin-coated 96-well microplate (Iwaki 4860-020) containing 150 μl of ES cell medium, and was cultured to extract the DNA for the recombinant test by PCR. 100 μl of liquid paraffin (sterilized with a 0.2 μm filter) was added to the remaining ES cells, and then the cells were stored frozen at −80° C. The ES cells for DNA extraction were cultured in the absence of the feeder cell, but ES cells for other purposes were always cultured with the feeder cells. The test for the recombinant was carried out by PCR as follows. Specifically, medium was removed from each well of the 96-well microplate where the cells had grown to confluence, Lysis buffer (5 μl 10×Taq buffer, 5 μl 5% NP-40, 4 μl Proteinase K, 36 μl H₂O) was added thereto, and the resulting mixture was incubated at 55° C. for 2 hours. The lysed sample was removed into a 0.5-ml tube, and then treated at 95° C. for 15 minutes. Subsequently, the sample was centrifuged at 10,000 rpm for 10 to 15 minutes, and 1 μl of the resulting supernatant was used as the template DNA for PCR analysis.

The PCR primers were designed to amplify a region of about 2.1 kb located between the 3' loxP in the homologous recombination vector and exon 10, which is not included in the homologous recombination vector.

Specifically, the PCR was carried out by using LOXP3 S2 primer (5'-CCGGTGTTCCACATAACTTC-3', SEQ ID NO:17) that contains the loxP sequence inserted in intron 8 and MPJ37 primer (5'-GTTTCCCAAGCTTTATTTATTGCC-3', SEQ ID NO:18) corresponding to the sequence of exon 10. The PCR condition was as follows:

Composition of the reaction solution

| 10x Ex Taq buffer (TaKaRa) | 5 μl |
| 2.5 mM dNTPs | 4 μl |
| ExTaq (TaKaRa) | 0.5 μl |
| 20 μM LOXP3 S2 primer | 1 μl |
| 20 μM MPJ37 primer | 1 μl |
| sample | 1 μl |
| H₂O | 37.5 μl |

Reaction condition

94° C., 2 min ->(94° C., 30 sec →68° C., 4 min)×36 cycles ->72° C., 10 min

Figure 8:
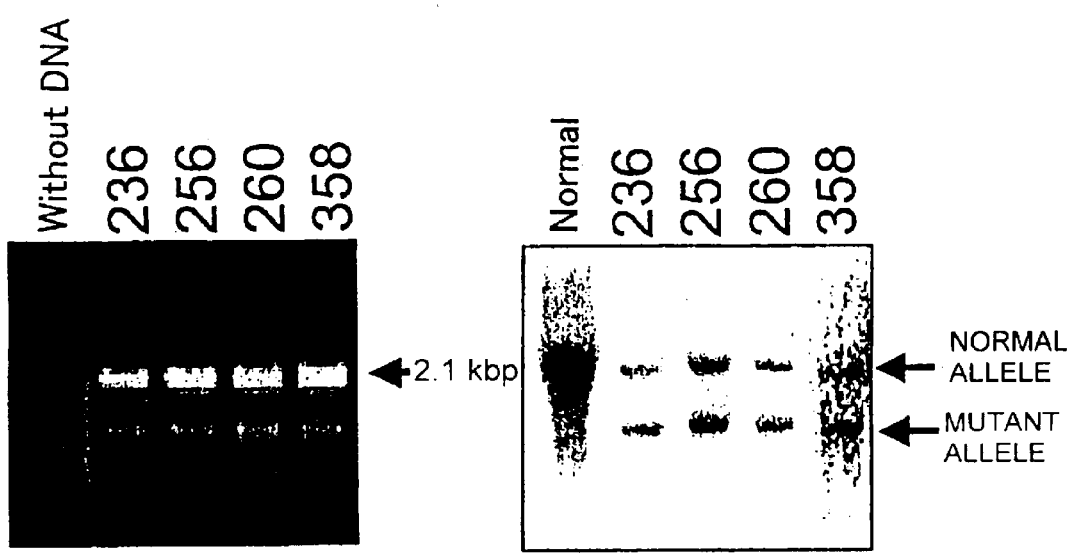
FIG. 8 shows photographs of the result of genotype testing of each ES cell clones. The presence of the recombinant mutant allele has been confirmed by the PCR analysis (left panel) and Southern blot analysis (right panel), respectively.

Clones estimated to be the recombinant based on the results of PCR were further verified by Southern blotting. Specifically, genomic DNA prepared from ES cells were digested with the restriction enzyme KpnI and then electrophoresed in a 0.8% agarose gel. The bands were transferred onto a Hybond N+ positive charged filter, (Amersham) and hybridization was performed using a fragment of about 700 bp containing exons 9 and 10 (probe 1) as a probe. Probe 1 was obtained by PCR amplification of clone 072 cosmid DNA as the template using MPJ22 primer (5'-CAGCAGCAAGGTGAAGCCAGAAGG-3', SEQ ID NO:19) and MPJ37 primer (SEQ ID NO:18) (above-mentioned). The hybridization was carried out by using ExpressHyb™ Hybridization solution (CLONTECH) according to the provider's instruction. The allele produced by homologous recombination yields a band that is about 2.6-kb shorter as compared to the wild-type allele, due to the presence of a KpnI site artificially added to the loxP sequence in the recombinant. The identification of the recombinant was based on the presence of this band. There were 4 recombinant clones (clone 236, clone 256, clone 260, and clone 358) among the tested 562 clones that were resistant to G418. The result of the PCR analysis was completely consistent with that by Southern blot analysis (FIG. 8).

Clones identified as products of homologous recombination by PCR and Southern blot analysis were thawed by incubation at 37° C. of the 96-well plate which had been stored in a frozen state, and then were passaged on a 24-well plate. The 24-well plate was incubated at 37° C. for 24 hours, and then the medium was changed to remove DMSO and liquid paraffin. When each of the clones had grown to 75–90% confluence, the cells were passaged from the 24-well plate to a 6-well plate. Further, when the cells in two wells had grown to 75–90% confluence in the 6-well plate, then the cells in one well were frozen and stored, and the cells in the other well were used for blastocyst injection and DNA extraction.

Cells were frozen and stored as follows. Specifically, cells were rinsed twice with ESQ PBS, and 0.5 μl of ESQ Trypsin (Lexicon, The Mouse Kit) was added thereto. After trypsin treatment at 37° C. for 15 to 20 minutes, 0.5 ml ES Cell medium was further added thereto, and the cells were completely dispersed into single cells by pipetting 35 to 40 times. This cell suspension was transferred into a 15-ml centrifuge tube, the well was further rinsed with another 1 ml of ES Cell Medium, and the wash solution was added to the same tube. The tube was centrifuged at 1,000 rpm for 7 minutes, and the medium was removed from the tube. The pellets were resuspended in 0.25 ml of ES Cell Medium, and 0.25 ml of 2×Freezing medium was added thereto. The content of the well was transferred into a cryogenic vial, was frozen at −80° C., and stored in liquid nitrogen.

ES cells to be used for blastocyst injection and DNA extraction were completely dispersed into single cells, then one quarter thereof was injected into blastocysts and the remaining one third and two third of the remaining cells were passaged into gelatin-coated 60-mm dishes, respectively. The former cells grown to confluence were used to extract genomic DNA for Southern blot analysis, and the latter cells grown to confluence were divided and frozen as three samples.

EXAMPLE 3

Preparation of Chimera Mice Using ES Cells Carrying the Recombinant LKB1 gene

Chimera embryos were prepared from ES cell clones, in which the occurrence of homologous recombination had been confirmed, using blastocysts from C57BL/6J mice as the host embryos. The chimera embryos were transplanted in the horn of uterus of pseudopregnant mouse to obtain newborns. The collection of host embryos was performed on the second day of pregnancy by perfusing the oviduct and uterus with Whitten's medium containing 100 μM EDTA. 8-cell embryos or morulae were cultured in Whitten's medium for 24 hours. The resulting blastocysts were used for the injection. ES cells to be used for the injection were passaged for 2 or 3 days and then dispersed by the treatment with TE. The cells were allowed to stand at 4° C. before microscopic manipulation.

The injection pipette used for ES cell manipulation was a polar body extrusion pipette (inner diameter of about 20 μm; Cook IVF). The holding pipette for embryo used was prepared by thinly drawing a micro glass tube (outer diameter of 1 mm; NARISHIGE) by using a device for preparation of microelectrodes (model P-98/IVF; Sutter), cutting vived (success rate=93%). These 55 blastocysts were transplanted into the horn of uterus of ICR recipient female on the second day of pseudopregnancy, which resulted in 28 newborns. The fur color of portions derived from the recombinant is a wild-type color and that in portions derived from the C57BL/6J mouse is black. 23 out of the resulting 28 newborns were judged to be chimera mice according to the fur color. 21 out of the 23 were morphologically male. Based on the fur color patterns of these chimera mice, the percentage of contribution of the ES cell ranges from 20 to 100%; there were 2 cases in which the contribution was less than 60%; 4 cases with a contribution of 60% or higher and less than 90%; 15 cases with a contribution higher than 90%. Similarly, chimera mice were also prepared from ES cells of clone 236 and clone 256. The result obtained for the preparation of chimera mice is shown in Table 1.

TABLE 1

| ES clone | Host embryo line | Number of injected embryos/ manipulated embryos | % | Number of transplated embryos | Number of implanted embryos | (%) | Number of newborns Total (%) | ♂ | ♀ | Number of mice with chimeric fur color Total (%) | ♂ | ♀ | Percentage of contribution |
|---|---|---|---|---|---|---|---|---|---|---|---|---|---|
| 236 | B6 | 70/74 | 95% | 70 | 46 | 66% | 24 34% | 17 | 7 | 12 50% | 10 | 2 | ♂ 6 animals, higher than 90%; 2 animals less than 90% and 60% or higher; 2 animals less than 60%. ♀ 2 animals, less than 60% |
| 256 | B6 | 57/58 | 98% | 57 | 44 | 77% | 20 39% | 11 | 9 | 4 18% | 4 | 0 | ♂ 3 animals, higher than 90%; 1 animal less than 90% and 60% or higher; 2 animals less than 60%. |
| 280 | B6 | 40/45 | 89% | 40 | 13 | 33% | 5 13% | 4 | 1 | 0 0% | — | — | |
| 358 | B6 | 55/59 | 93% | 55 | — | — | 28 51% | 22 | 6 | 23 82% | 21 | 2 | ♂ 15 animals, higher than 90%; 4 animals less than 90% and 60% or higher; 2 animals less than 60%. ♀ 2 animals, less than 60% | the extended tube with a microforge (De Fonburun) at a position where the outer diameter is 50 to 100 μm, and further processing it to narrow the gauge thereof down to 10 to 20 μm.

Both of the injection pipette and holding pipette were bent to an angle of about 30 degrees at the position of about 5 mm from the tip, and then attached to a micromanipulator (LEITZ). A depression glass slide to which the cover glass is glued with yellow wax was used as the chamber for manipulation under the microscope, and two drops of Hepes-buffered Whitten's medium containing about 20 μl of 0.3% BSA were separately placed thereon. The surfaces of the drops were covered with liquid paraffin (Nacalai tesque; 261-37 SP). About 100 ES cells were placed in one drop, and 10 to 15 expanded blastocysts in the other drop. 10 to 15 ES cells were injected into each embryo.

All microscopic manipulation was carried out under the inverted microscope. After culturing for 1 to 2 hours, the manipulated embryos were transplanted into the horn of uterus of ICR recipient females on the second day of pseudopregnancy. When no newborns were delivered on the expected date of delivery, the recipient female mouse was subjected to Caesarean operation, and foster mothers were used to take care of the newborns.

ES cells of clone 358 were injected into 59 blastocysts from C57BL/6J mice. Among the 59, 55 blastocysts sur-

EXAMPLE 4

Evaluation of Germline Transmission of Recombinant Cells

Each of the chimera mice prepared in Example 3 was mated with a C57BL/6J mouse in order to evaluate whether or not ES cell derived newborns are obtainable. When the germline cell in a chimera mouse is derived from the ES cell, then fur color of the newborn has a wild-type color, whereas the color is black when the germline cell is derived from the blastocyst of C57BL/6J mouse.

Transmission of the ES-cell to the germline was verified in 6 animals (No. 358-1, 2, 5, 7, 8, 13) of 16 chimera mice (No. 358-1 to 358-16) utilizing ES cells of clone 358. 5 animals died before they reached sexual maturity, and they were excluded from the numbers above. The number of newborns having the wild-type color in the newborns obtained in these 6 mice was 7 in 9, 2 in 2, 3 in 14, 8 in 8, 5 in 16, and 2 in 11, respectively. Transmission of the ES-cell to the germline was also verified in 2 animals (No. 256-1 and -2) of 4 chimera mice (No. 256-1 to 256-4) utilizing ES cells of clone 256. The number of newborns having the wild-type color in the newborns obtained was 2 in 3 and 1 in 13, respectively.

Subsequently, DNA was extracted from a part of the tail of 27 mice selected from mice having the wild-type color.

Figure 9:
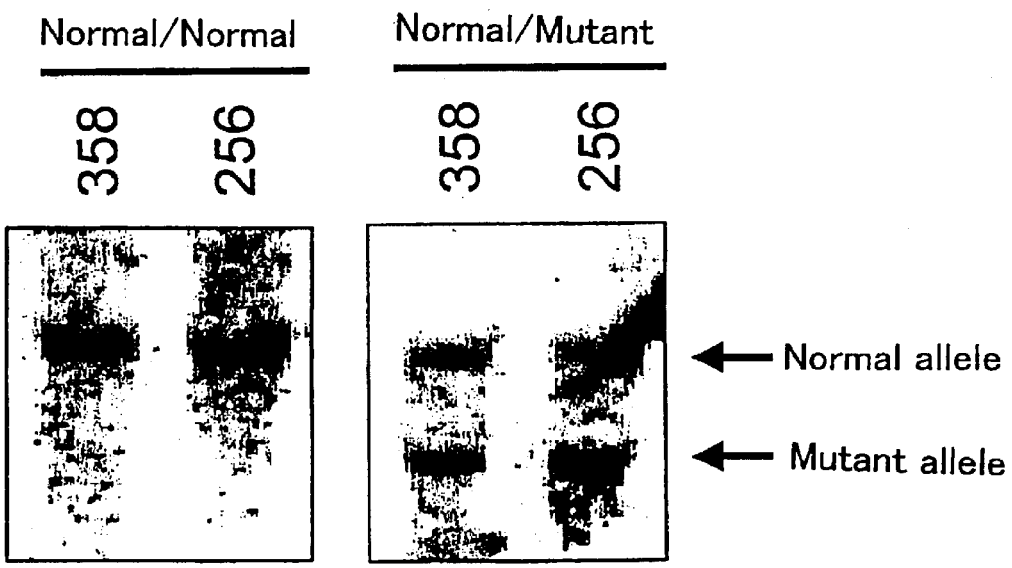
FIG. 9 shows a photograph of genotype testing by Southern blotting of the F1 mice obtained by mating the chimera mice. A band for the mutant allele together with that of the normal allele is seen in the mice shown on the right panel, demonstrating that the mutant allele in ES cell has been transmitted to the F1 mice. Indicated numerals correspond to ES cell clones from which each mouse had been derived.

Transmission of the mutated LKB1 allele was determined by PCR and Southern blotting. The result showed that transmission of the mutated LKB1 allele was achieved in 10 newborns derived from clone 358 ES cell and one from clone 256 ES cell (FIG. 9).

The above-described result for transmission of the mutant allele is shown in Table 2.

TABLE 2

The result for transmission of the mutant allele

| Chimera mouse No. | ES clone | Number of newborns | Number of positive animals | | |
|---|---|---|---|---|---|
| | | | Fur color | PCR | Southern blot |
| 358-1 | 358 | 9 | 7 | 0 | — |
| 358-2 | 358 | 2 | 2 | 2 | 2 |
| 358-3 | 358 | 6 | 0 | — | — |
| 358-4 | 358 | 3 | 0 | — | — |
| 358-5 | 358 | 14 | 3 | 0 | — |
| 358-6 | 358 | 14 | 0 | — | — |
| 358-7 | 358 | 8 | 8 | 3 | 3 |
| 358-8 | 358 | 16 | 5 | 5 | 5 |
| 358-9 | 358 | 1 | 0 | — | — |
| 358-10 | 358 | 8 | 0 | — | — |
| 358-11 | 358 | — | — | — | — |
| 358-12 | 358 | 6 | — | — | — |
| 358-13 | 358 | 11 | 2 | — | — |
| 358-14 | 358 | — | — | — | — |
| 358-15 | 358 | — | — | — | — |
| 358-16 | 358 | — | — | — | — |
| 256-1 | 256 | 3 | 2 | 1 | 1 |
| 256-2 | 256 | 13 | 1 | 0 | — |
| 256-3 | 256 | 7 | 0 | — | — |
| 256-4 | 256 | — | — | — | — |
| total | | 121 | 30 | 11 | 11 |

EXAMPLE 5

Inactivation of the LKB1 Gene by Cre-loxP System

Figure 5:
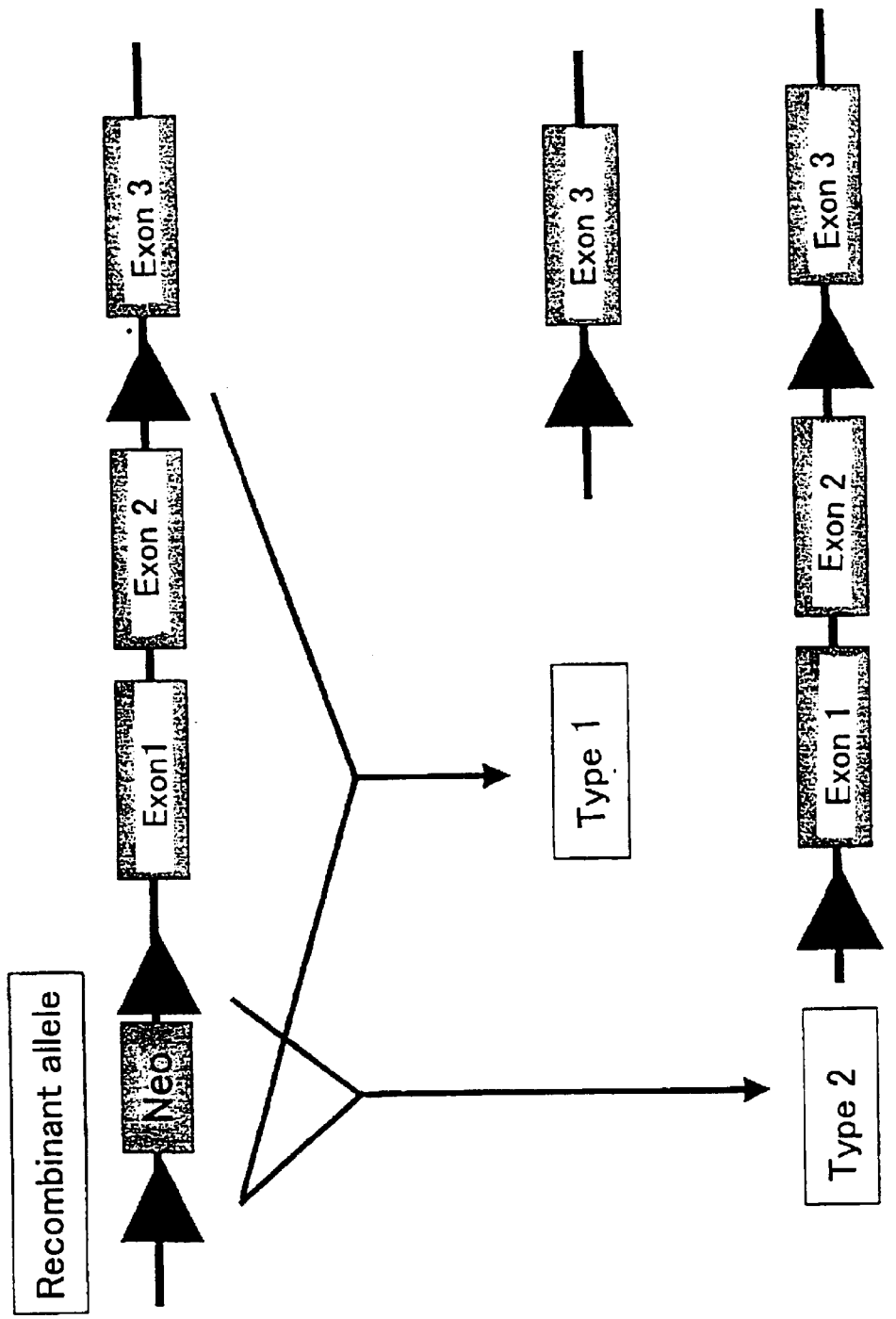
FIG. 5 shows an example of application of the Cre-loxP system. Closed triangle represents the loxP sequence. The expression of Cre recombinase results in site-specific homologous recombination, which provides two genotypes (type 1 and type 2).

ES cells carrying conventional gene deletion as well as ES cells carrying conditional gene deletion can be prepared by transiently expressing the Cre gene in ES cells (Taniguchi, M et al. Nucleic Acids Research 26: 679–680, 1998). The animal derived from an ES cell carrying the conditional-type deletion (type 2, FIG. 5) exhibits wild-type phenotypes; however, the LKB1 gene can be inactivated by expressing the Cre gene.

Furthermore, this system can be utilized to disrupt functions of the LKB1 gene. It can be achieved by deleting the region covering exons 2 to 8 of the LKB1 gene specifically inserted between the loxP sequences in cells expressing the Cre gene, which expression of the Cre is achieved by mating the above system with a transgenic mouse in which the Cre gene is regulated by a promoter capable of regulating gene expression in a tissue-specific or phase-specific manner, or alternatively by infecting with a recombinant adenovirus capable of expressing the Cre gene. Thus, in the Cre-loxP system, the gene inserted between the loxP sequences can be deleted through recombination by expressing the Cre gene in ES cell, mouse individual, or mouse fertilized egg in a phase-specific manner or in a tissue-specific manner.

EXAMPLE 6

Preparation and the Phenotype of LKB1 Gene Deficient Mouse Utilizing the Cre-loxP system In vitro fertilization (Toyoda Y et al., Jpn. J. Anim. Reprod. 16:147–151, 1971) was performed by using sperms from clone 358 male mouse, which was verified to carry the LKB1 mutant allele of ES cell, and eggs from C57BL/6J mouse to obtain the egg at pronucleus stage (at this stage, the LKB1 structural gene corresponded to the state of the recombinant allele described in FIG. 10). The plasmid pCre-pac in which the expression of the Cre gene is regulated by the MC1 promoter (Taniguchi et al., Nucleic Acids Res. 26:679–680, 1998) was injected in a circular form (Araki et al., Proc. Natl. Acad. Sci. USA 92:160–164, 1995) into the pronucleus of the egg at the pronucleus stage. The injunction was carried out with 86 fertilized eggs, and 75 of these eggs survived after the injection. Then, the fertilized eggs were cultured in Whitten's medium containing 100 μM EDTA for 24 hours. 61 eggs that proceeded to the 2-cell stage were transplanted into the oviduct of recipient female ICR mice on day 0.5 of pseudopregnancy. 12 newborns were obtained. All of them survived beyond the weaning period. DNA was extracted from a part of the tail from each of the weaned mice, and then tested by PCR to select animals in which a region from exon 2 to exon 8 of the LKB1 gene inserted between the loxP sequences was deleted. PCR was performed as follows:

Primer set set A: MPJ69 primer (5'-CCTTTGGCTGCTGGGTGACTTCTG-3', SEQ ID NO:20) and MPJ37 primer (SEQ ID NO:18)

set B: MPJ69 primer (SEQ ID NO:20) and MPJ56 primer (5'-ACAGAGCTCTCCAAGGGAGA-3', SEQ ID NO:21)

Composition of the reaction solution

| 10x ExTaq buffer (TaKaRa) | 5 μl |
| 2.5 mM dNTPs | 4 μl |
| ExTaq (TaKaRa) | 0.5 μl |
| anti-Taq antibody (CLONTECH) | 0.5 μl |
| 20 μM forward primer | 1 μl |
| 20 μM reverse primer | 1 μl |
| sample | 1 μl |
| H₂O | 37 μl |

Reaction condition

94° C., 2 min →(94° C., 30 sec →68° C., 3 min)×35 cycles →72° C., 10 min

Figure 10:
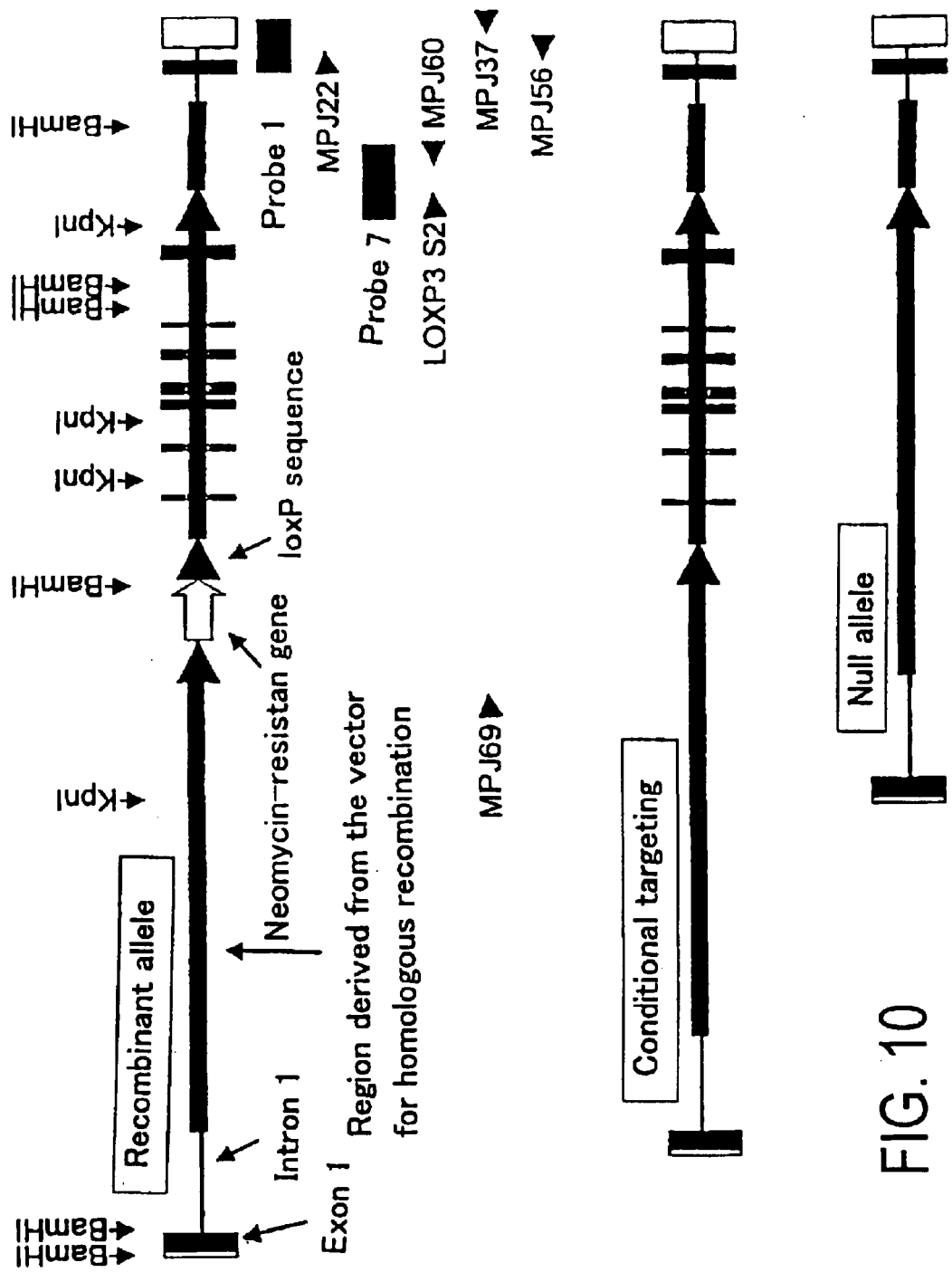
FIG. 10 is a schematic illustration of the recombinant allele, conditional allele, and null allele. Relative positions of the respective primers and probes are shown.
Figure 11A:
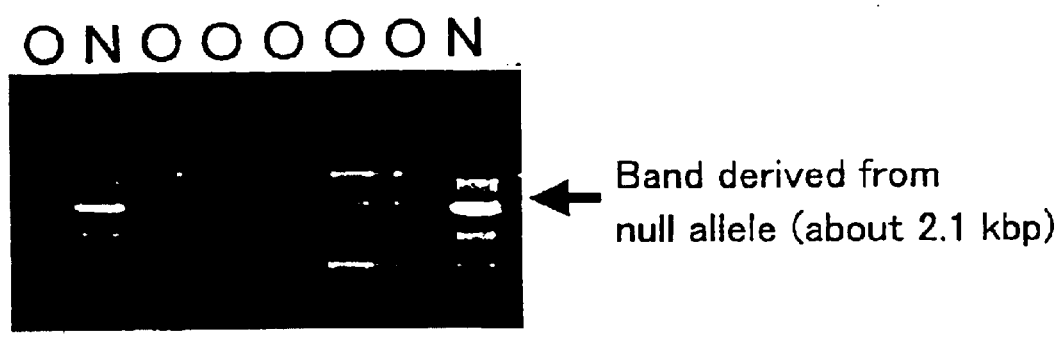
FIG. 11—Panel A is a photograph showing the result of PCR using the primer set (set A) used for detecting the null allele. N denotes a sample showing the band (about 2.1 kbp) corresponding to the null allele; O, a sample showing other alleles.
Figure 11B:
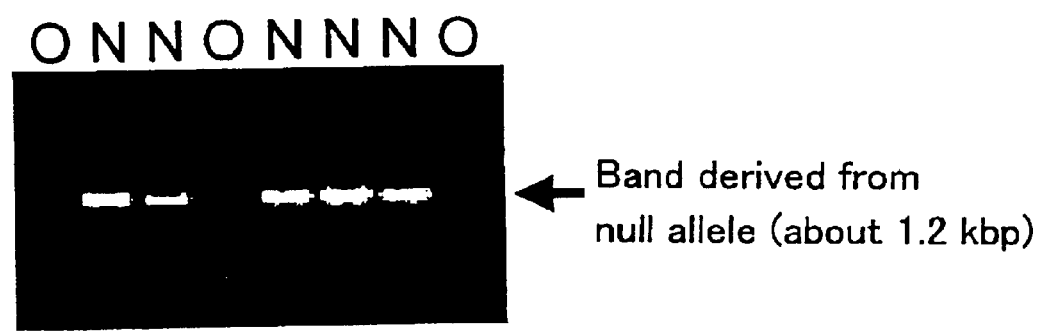
Figure 11C:
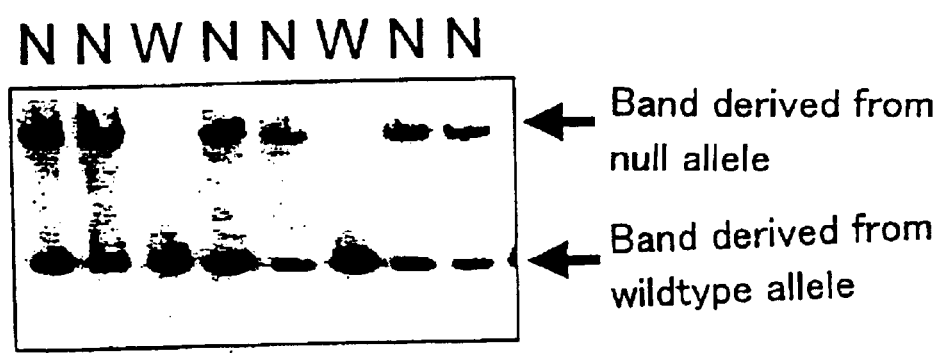

A band of about 2.1 kbp was observed for samples from some mice by PCR with primer set A (FIG. 11A). The size of this band was as expected for a DNA wherein the region from exon 2 to exon 8 inserted between the loxP sequences has been deleted (FIG. 10). These mice were judged to have the null allele and were used for the following analysis. In vitro fertilization was performed by using sperms from male mouse carrying the null allele (heterozygous deficiency) and eggs from C57BL/6J mouse. The resulting fertilized eggs were transplanted into the oviduct of recipient female ICR mice on day 0.5 of pseudopregnancy to obtain newborns (F1). Genomic DNA was extracted from a part of the tail from each of the F1 mice, and then the DNA samples was tested by PCR using the primer set B to select mouse with heterozygous deficiency to which the null allele had been transmitted (FIG. 11B). When primer set B was used, the size of band amplified from the null allele is expected to be about 1.2 kbp (FIG. 10). Mouse individuals showing the band of this size were judged to have the null allele. The sequence of this 1.2-kbp band was directly determined for some samples to confirm that the band is derived from the null allele produced by the expected deletion. Subsequently, in order to create F2 mouse homozygous for the null allele, in vitro fertilization was performed by using sperms and eggs from the F1 mice with heterozygous deficiency. Genotypes of the F2 mice prepared by transplanting the fertilized eggs in pseudopregnant female mice were analyzed by Southern blotting. Genomic DNA extracted from the tail of each mouse was digested with BamHI, and then was subjected to hybridization using probe 7 (FIG. 10) corresponding to a part of intron 8 as a probe. Probe 7 was obtained by the PCR amplification using LOXP3 S2 primer (SEQ ID NO:17) and MPJ60 primer (5'-CTCTCCCAAACCCTCTGACT-3', SEQ ID NO:22), and the vector for homologous recombination (LT6) as the template. The hybridization was carried out by using ULTRAhyb™ (Ambion) according to the provider's instruction. It was expected that a band of about 2kbp placed between the two BamHI sites located in intron 7 and intron 8 will be observed for the wild-type allele, and a band longer than 7kbp containing intron 1 for the null allele due to the absence of a BamHI site in intron 7 (FIG. 10). A part of the results obtained by Southern blotting is shown in FIG. 11C. All the samples share the same band derived from the wild-type allele, and some samples shows the longer band corresponding to the null allele. The result of Southern blot analysis showed a ratio of 55:90:0 for the number of homozygous mice with the wild-type alleles: heterozygous mice with a null allele: homozygous mice with the null alleles. The result revealed that the LKB1 gene deficiency results in embryonic lethality in mouse. Accordingly, the LKB1 gene was considered to be an essential gene in embryogenesis.

INDUSTRIAL APPLICABILITY

The present invention provides mammals in which the expression of the LKB1 gene can be artificially suppressed or is artificially suppressed. The LKB1 gene can be disrupted in a phase-specific or tissue-specific manner in the mammals of the present invention, for example, by using the Cre-loxP system. The present invention enables one to overcome the previously recognized serious problem of embryonic lethality caused by inactivation of the gene and, thereby, allows one to further analyze an object gene which functional analysis was previously impossible. The mammals of the present invention are expected to be highly useful as tools to reveal the onset mechanism of a variety of diseases caused by LKB1 gene deficiency, such as human PJS and cancers, as well as to develop therapeutic agents, methods, and so on for the diseases.

What is claimed is:

1. A transgenic postnatal mouse whose genome comprises a heterozygous disruption in the LKB1 gene as a result of recombinase mediated gene disruption prior to embryogenesis, wherein the mouse exhibits digestive tract polyposis.

2. The transgenic postnatal mouse of claim 1, wherein the recombinase is Cre.

3. The transgenic postnatal mouse of claim 1, wherein the recombinase is Flp.

* * * * *